United States Patent [19]
Goelet et al.

[11] Patent Number: 5,888,819
[45] Date of Patent: Mar. 30, 1999

[54] METHOD FOR DETERMINING NUCLEOTIDE IDENTITY THROUGH PRIMER EXTENSION

[75] Inventors: Philip Goelet, Cockeysville; Michael R. Knapp, Baltimore, both of Md.; Stephen Anderson, Princeton, N.J.

[73] Assignee: Molecular Tool, Inc., Baltimore, Md.

[21] Appl. No.: 664,837

[22] Filed: Mar. 5, 1991

[51] Int. Cl.[6] ............... C12Q 1/70; C12Q 1/68; C12P 19/34
[52] U.S. Cl. ............... 435/5; 435/6; 435/91.2
[58] Field of Search ............... 435/5, 91, 6, 91.2; 935/76, 77, 78

[56] References Cited

U.S. PATENT DOCUMENTS

| | | | |
|---|---|---|---|
| 4,656,127 | 4/1987 | Mundy | 435/6 |
| 4,962,020 | 10/1990 | Tabor et al. | 435/6 |

OTHER PUBLICATIONS

K. B. Mullis, Scientific American, (Apr. 1990), "The Unusual Origin of the Polymerase Chain Reaction", pp. 56–65.

Prober et al. (1987) Science, vol. 238, pp. 336–341.

*Primary Examiner*—Lisa B. Arthur
*Attorney, Agent, or Firm*—Howrey & Simon; Jeffrey I. Auerbach

[57] ABSTRACT

The invention concerns a reagent composition that employs at least two different terminators of a nucleic acid template-dependent primer extension reaction to determine the identity of a nucleotide base at a specific position in a nucleic acid of interest. The invention also concerns the method for determining such identification. The invention may be used to determine the presence or absence of a specific nucleotide sequence in a sample. It may also be employed in determination of genotype and in the identification of different alleles.

48 Claims, 8 Drawing Sheets

I. Amplification primers

TGL 105:    5'-TTCTTCTTGCATCTATGTTCG-3'

TGL 106:    5'-TTAAGCACCACCACAGGTCCT-3'

II. Polymorphism detection primers

TGL 182:    5'-GCCTTGGCGTTGTAGAA-3'

TGL 166:    5'-AGAGAAACAATTTCAAG-3'

III. Target sequence

```
5'   ...TTTCTTCTTG CATCTATGTT CGTTTTTTCT ATTGCTACAA    40
            TGL 105 ----->
        ATGCCTATGC ACGGCCTGAC TTCTGCCTAG AGCCTCCATA    80
                                             C
        TACGGGTCCC TGCAAGGCCA GAATTATCAG ATA /TTTCTAC  120

AACGCCAAGG CTGGGCTCTG CCAGACCTTT GTATATGGTG   160
        <----- TGL 182
                                                A
        GCTGCAGAGC TAAGAGAAAC AATTTCAAG /G GCGCAGAGGA  200
                       TGL 166 ----->

CTGCATGAGG ACCTGTGGTG GTGCTTAAGG GCCCCCGGGAA...3' 240
                   <----- TGL 106
```

IV. Polymorphisms

| Plasmid | Nucleotide 114 | Nucleotide 190 |
|---------|---------------|----------------|
| p183    | C             | A              |
| p624    | T             | A              |
| p814    | C             | G              |

FIG.2

```
                                    Attached to bead
                                     ┌─
                                     └─ 5' AGATGATGCT TTTGTGCAAA ACACTTTTTA ACACCTCTTT TAAAATTTCT TTCAAATTCT ACGGCATTTT
                                           TGL240 (PCR Primer with Biotin)

TTTCCTGAAA ATGCTTCGGT TTTAGGTCAA AGCTTTATTC TCCTAAGAAC CTAACTCCCA CTGGTCTCAG

GCGCCCTCTC GGAGCCCTCG GGAGTCTTT GCCCCCCAAT CTTGGCATTC TCCCCTGACA CTCGCCCAAG

TGL308 5'
                                                                  3' TGGTCCGT GGTGCGCCAG ACTCCGA
                                        GCCCCTAACC TGCACCCGGG CACCAGGCA CCACGCGGGTC TGAGGCTTCA GCAGGGAAGG CCTGCTCTCC
                                                                GA                                           T  C      B allele
                                                                                                                        differences TGL239 (Non-biotinylated PCR Primer)
                                                    3' GTCCCAC AGCCCTGAGT CCATAACT 5'
                                        GTTCACACTG CTTTCAGGCC CGGCAGGGTG TCGGGACTCA GGTATTGA 3'
```

METHOD FOR DETERMINING NUCLEOTIDE IDENTITY THROUGH PRIMER EXTENSION

BACKGROUND OF THE INVENTION

This invention relates to the field of nucleic acid sequence detection. The detection of nucleic acid sequences can be used in two general contexts. First, the detection of nucleic acid sequences can be used to determine the presence or absence of a particular genetic element. Second, the detection of nucleic acid sequences can be used to determine the specific type of a particular genetic element that is present. Variant genetic elements usually exist. Many techniques have been developed (1) to determine the presence of specific nucleic acid sequences, and (2) to compare homologous segments of nucleic acid sequence to determine if the segments are identical or if they differ at one or more nucleotides. Practical applications of these techniques include genetic disease diagnoses, infectious disease diagnoses, forensic techniques, paternity determinations, and genome mapping.

In general, the detection of nucleic acids in a sample and the subtypes thereof depends on the technique of specific nucleic acid hybridization in which the oligonucleotide probe is annealed under conditions of high stringency to nucleic acids in the sample, and the successfully annealed probes are subsequently detected (see Spiegelman, S., *Scientific American*, Vol. 210, p. 48 (1964)).

The most definitive method for comparing DNA segments is to determine the complete nucleotide sequence of each segment. Examples of how sequencing has been used to study mutations in human genes are included in the publications of Engelke, et al., *Proc. Natl. Acad. Sci. U.S.A.*, 85:544–548 (1988) and Wong, et al., *Nature*, 330:384–386 (1987). At the present time, it is not practical to use extensive sequencing to compare more than just a few DNA segments because the effort required to determine, interpret, and compare sequence information is time-consuming.

A commonly used screen for DNA polymorphisms arising from DNA sequence variation consists of digesting DNA with restriction endonucleases and analyzing the resulting fragments by means of Southern blots, as described by Botstein, et al., *Am. J. Hum. Genet.*, 32:314–331 (1980) and White, et al., *Sci. Am.*, 258:40–48 (1988). Mutations that affect the recognition sequence of the endonuclease will preclude enzymatic cleavage at that site, thereby altering the cleavage pattern of that DNA. DNAs are compared by looking for differences in restriction fragment lengths. A major problem with this method (known as restriction fragment length polymorphism mapping or RFLP mapping) is its inability to detect mutations that do not affect cleavage with a restriction endonuclease. Thus, many mutations are missed with this method. One study, by Jeffreys, *Cell*, 18:1–18 (1979), was able to detect only 0.7% of the mutational variants estimated to be present in a 40,000 base pair region of human DNA. Another problem is that the methods used to detect restriction fragment length polymorphisms are very labor intensive, in particular, the techniques involved with Southern blot analysis.

A technique for detecting specific mutations in any segment of DNA is described in Wallace, et al., *Nucl. Acids Res.*, 9:879–894 (1981). It involves hybridizing the DNA to be analyzed (target DNA) with a complementary, labeled oligonucleotide probe. Due to the thermal instability of DNA duplexes containing even a single base pair mismatch, differential melting temperature can be used to distinguish target DNAs that are perfectly complementary to the probe from target DNAs that differ by as little as a single nucleotide. In a related technique, described in Landegren, et al., *Science*, 41:1077–1080 (1988), oligonucleotide probes are constructed in pairs such that their junction corresponds to the site on the DNA being analyzed for mutation. These oligonucleotides are then hybridized to the DNA being analyzed. Base pair mismatch between either oligonucleotide and the target DNA at the junction location prevents the efficient joining of the two oligonucleotide probes by DNA ligase.

A. Nucleic acid hybridization

The base pairing of nucleic acids in a hybridization reaction forms the basis of most nucleic acid analytical and diagnostic techniques. In practice, tests based only on parameters of nucleic acid hybridization function poorly in cases where the sequence complexity of the test sample is high. This is partly due to the small thermodynamic differences in hybrid stability, generated by single nucleotide changes, and the fact that increasing specificity by lengthening the probe has the effect of further diminishing this differential stability. Nucleic acid hybridization is, therefore, generally combined with some other selection or enrichment procedure for analytical and diagnostic purposes.

Combining hybridization with size fractionation of hybridized molecules as a selection technique has been one general diagnostic approach. Size selection can be carried out prior to hybridization. The best known prior size selection technique is Southern Blotting (see Southern, E., *Methods in Enzymology*, 69:152 (1980). In this technique, a DNA sample is subjected to digestion with restriction enzymes which introduce double stranded breaks in the phosphodiester backbone at or near the site of a short sequence of nucleotides which is characteristic for each enzyme. The resulting heterogeneous mixture of DNA fragments is then separated by gel electrophoresis, denatured, and transferred to a solid phase where it is subjected to hybridization analysis in situ using a labeled nucleic acid probe. Fragments which contain sequences complementary to the labeled probe are revealed visually or densitometrically as bands of hybridized label. A variation of this method is Northern Blotting for RNA molecules. Size selection has also been used after hybridization in a number of techniques, in particular by hybrid protection techniques, by subjecting probe/nucleic acid hybrids to enzymatic digestion before size analysis.

B. Polymerase extension of duplex primer:template complexes

Hybrids between primers and DNA targets can be analyzed by polymerase extension of the hybrids. A modification of this methodology is the polymerase chain reaction in which the purification is produced by sequential hybridization reactions of anti-parallel primers, followed by enzymatic amplification with DNA polymerase (see Saiki, et al., *Science* 239:487–491 (1988)). By selecting for two hybridization reactions, this methodology provides the specificity lacking in techniques that depend only upon a single hybridization reaction.

It has long been known that primer-dependent DNA polymerases have, in general, a low error rate for the addition of nucleotides complementary to a template. This feature is essential in biology for the prevention of genetic mistakes which would have detrimental effects on progeny. The specificity inherent in this enzymological reaction has been widely exploited as the basis of the "Sanger" or dideoxy chain termination sequencing methodology which is the ultimate nucleic acid typing experiment. One type of Sanger DNA sequencing method makes use of mixtures of the four deoxynucleoside triphosphates, which are normal DNA precursors, and one of the four possible dideoxynucleoside triphosphates, which have a hydrogen atom instead of a hydroxyl group attached to the 3' carbon atom of the ribose sugar component of the nucleotide. DNA chain elongation in the 5' to 3' direction ("downstream") requires this hydroxyl group. As such, when a dideoxynucleotide is incorporated into the growing DNA chain, no further elongation can occur. With one dideoxynucleotide in the mixture, DNA polymerases can, from a primer:template combination, produce a population of molecules of varying length, all of which terminate after the addition of one out of the four possible nucleotides. The series of four independent reactions, each with a different dideoxynucleotide, generates a nested set of fragments, all starting at the same 5' terminus of the priming DNA molecule and terminating at all possible 3' nucleotide positions.

Another utilization of dideoxynucleoside triphosphates and a polymerase in the analysis of DNA involves labeling the 3' end of a molecule. One prominent manifestation of this technique provides the means for sequencing a DNA molecule from its 3' end using the Maxam-Gilbert method. In this technique, a molecule with a protruding 3' end is treated with terminal transferase in the presence of radioactive dideoxy-ATP. One radioactive nucleotide is added, rendering the molecule suitable for sequencing. Both methods of DNA sequencing using labeled dideoxynucleotides require electrophoretic separation of reaction products in order to derive the typing information. Most methods require four separate gel tracks for each typing determination.

The following two patents describe other methods of typing nucleic acids which employ primer extension and labeled nucleotides. Mundy (U.S. Pat. No. 4,656,127) describes a method whereby a primer is constructed complementary to a region of a target nucleic acid of interest such that its 3' end is close to a nucleotide in which variation can occur. This hybrid is subject to primer extension in the presence of a DNA polymerase and four deoxynucleoside triphosphates, one of which is an α-thionucleotide. The hybrid is then digested using an exonuclease enzyme which cannot use thio-derivatized DNA as a substrate for its nucleolytic action (for example Exonuclease III of *E. coli*). If the variant nucleotide in the template is complementary to one of the thionucleotides in the reaction mixture, the resulting extended primer molecule will be of a characteristic size and resistant to the exonuclease; hybrids without thio-derivatized DNA will be digested. After an appropriate enzyme digest to remove underivatized molecules, the thio-derivatized molecule can be detected by gel electrophoresis or other separation technology.

Vary and Diamond (U.S. Pat. No. 4,851,331) describes a method similar to that of Mundy wherein the last nucleotide of the primer corresponds to the variant nucleotide of interest. Since mismatching of the primer and the template at the 3' terminal nucleotide of the primer is counterproductive to elongation, significant differences in the amount of incorporation of a tracer nucleotide will result under normal primer extension conditions. This method depends on the use of a DNA polymerase, e.g., AMV reverse transcriptase, that does not have an associated 3' to 5' exonuclease activity. The methods of Mundy and of Vary and Diamond have drawbacks. The method of Mundy is useful but cumbersome due to the requirements of the second, different enzymological system where the non-derivatized hybrids are digested. The method of Vary is complicated by the fact that it does not generate discrete reaction products. Any "false" priming will generate significant noise in such a system which would be difficult to distinguish from a genuine signal.

The present invention circumvents the problems associated with the methods of Mundy and of Vary and Diamond for typing nucleic acid with respect to particular nucleotides. With methods employing primer extension and a DNA polymerase, the current invention will generate a discrete molecular species one base longer than the primer itself. In many methods, particularly those employing the polymerase chain reaction, the type of reaction used to purify the nucleic acid of interest in the first step can also be used in the subsequent detection step. Finally, with terminators which are labeled with different detector moieties (for example different fluorophors having different spectral properties), it will be possible to use only one reagent for all sequence detection experiments. Furthermore, if techniques are used to separate the terminated primers post-reaction, sequence detection experiments at more than one locus can be carried out in the same tube.

A recent article by Mullis (*Scientific American*, April 1990, pp. 56–65) suggests an experiment, which apparently was not performed, to determine the identity of a targeted base pair in a piece of double-stranded DNA. Mullis suggests using four types of dideoxynucleosides triphosphate, with one type of dideoxynucleoside triphosphate being radioactively labeled.

The present invention permits analyses of nucleic acid sequences that can be useful in the diagnosis of infectious diseases, the diagnosis of genetic disorders, and in the identification of individuals and their parentage.

A number of methods have been developed for these purposes. Although powerful, such methodologies have been cumbersome and expensive, generally involving a combination of techniques such as gel electrophoresis, blotting, hybridization, and autoradiography or non-isotopic revelation. Simpler technologies are needed to allow the more widespread use of nucleic acid analysis. In addition, tests based on nucleic acids are currently among the most expensive of laboratory procedures and for this reason cannot be used on a routine basis. Finally, current techniques are not adapted to automated procedures which would be necessary to allow the analysis of large numbers of samples and would further reduce the cost.

The current invention provides a method that can be used to diagnose or characterize nucleic acids in biological samples without recourse to gel electrophoretic size separation of the nucleic acid species. This feature renders this process easily adaptable to automation and thus will permit the analysis of large numbers of samples at relatively low cost. Because nucleic acids are the essential blueprint of life, each organism or individual can be uniquely characterized by identifiable sequences of nucleic acids. It is, therefore, possible to identify the presence of particular organisms or demonstrate the biological origin of certain samples by detecting these specific nucleic acid sequences.

SUMMARY OF THE INVENTION

The subject invention provides a reagent composition comprising an aqueous carrier and an admixture of at least two different terminators of a nucleic acid template-dependent, primer extension reaction. Each of the terminators is capable of specifically terminating the extension reaction in a manner strictly dependent on the identity of the unpaired nucleotide base in the template immediately adjacent to, and downstream of, the 3' end of the primer. In addition, at least one of the terminators is labeled with a detectable marker.

The subject invention further provides a reagent composition comprising an aqueous carrier and an admixture of four different terminators of a nucleic acid template-dependent, primer extension reaction. Each of the terminators is capable of specifically terminating the extension reaction as above and one, two, three, or four of the terminators is labeled with a detectable marker.

The subject invention further provides a reagent as described above wherein the terminators comprise nucleotides, nucleotide analogs, dideoxynucleotides, or arabinoside triphosphates. The subject invention also provides a reagent wherein the terminators comprise one or more of dideoxyadenosine triphosphate (ddATP), dideoxycytosine triphosphate (ddCTP), dideoxyguanosine triphosphate (ddGTP), dideoxythymidine triphosphate (ddTTP), or dideoxyuridine triphosphate (ddUTP).

The subject invention also provides a method for determining the identity of a nucleotide base at a specific position in a nucleic acid of interest. First, a sample containing the nucleic acid of interest is treated, if such nucleic acid is double-stranded, so as to obtain unpaired nucleotide bases spanning the specific position. If the nucleic acid of interest is single-stranded, this step is not necessary. Second, the sample containing the nucleic acid of interest is contacted with an oligonucleotide primer under hybridizing conditions. The oligonucleotide primer is capable of hybridizing with a stretch of nucleotide bases present in the nucleic acid of interest, immediately adjacent to the nucleotide base to be identified, so as to form a duplex between the primer and the nucleic acid of interest such that the nucleotide base to be identified is the first unpaired base in the template immediately downstream of the 3' end of the primer in the duplex of primer and the nucleic acid of interest. Enzymatic extension of the oligonucleotide primer in the resultant duplex by one nucleotide, catalyzed, for example, by a DNA polymerase, thus depends on correct base pairing of the added nucleotide to the nucleotide base to be identified.

The duplex of primer and the nucleic acid of interest is then contacted with a reagent containing four labeled terminators, each terminator being labeled with a different detectable marker. The duplex of primer and the nucleic acid of interest is contacted with the reagent under conditions permitting base pairing of a complementary terminator present in the reagent with the nucleotide base to be identified and the occurrence of a template-dependent, primer extension reaction so as to incorporate the terminator at the 3' end of the primer. The net result is that the oligonucleotide primer has been extended by one terminator. Next, the identity of the detectable marker present at the 3' end of the extended primer is determined. The identity of the detectable marker indicates which terminator has base paired to the next base in the nucleic acid of interest. Since the terminator is complementary to the next base in the nucleic acid of interest, the identity of the next base in the nucleic acid of interest is thereby determined.

The subject invention also provides another method for determining the identity of a nucleotide base at a specific position in a nucleic acid of interest. This additional method uses a reagent containing four terminators, only one of the terminators having a detectable marker.

The subject invention also provides a method of typing a sample of nucleic acids which comprises identifying the base or bases present at each of one or more specific positions, each such nucleotide base being identified using one of the methods for determining the identity of a nucleotide base at a specific position in a nucleic acid of interest as outlined above. Each specific position in the nucleic acid of interest is determined using a different primer. The identity of each nucleotide base or bases at each position can be determined individually or the identities of the nucleotide bases at different positions can be determined simultaneously.

The subject invention further provides a method for identifying different alleles in a sample containing nucleic acids which comprises identifying the base or bases present at each of one or more specific positions. The identity of each nucleotide base is determined by the method for determining the identity of a nucleotide base at a specific position in a nucleic acid of interest as outlined above.

The subject invention also provides a method for determining the genotype of an organism at one or more particular genetic loci which comprises obtaining from the organism a sample containing genomic DNA and identifying the nucleotide base or bases present at each of one or more specific positions in nucleic acids of interest. The identity of each such base is determined by using one of the methods for determining the identity of a nucleotide base at a specific position in a nucleic acid of interest as outlined above. The identities of the nucleotide bases determine the different alleles and, thereby, determine the genotype of the organism at one or more particular genetic loci.

BRIEF DESCRIPTION OF THE FIGURES

FIG. 2. Detection of Sequence Polymorphisms in PCR Products. Target polymorphic DNA sequence (SEQ ID NO:13) showing amplification primers, detection primers, and molecular clone (plasmid) designations. For each primer, sites of binding to one or the other strand of the target DNA sequence are indicated by underlining, and the direction of DNA synthesis is indicated by an arrow. Numbering for the target sequence is shown in the righthand margin. Polymorphic sites at positions 114 and 190 are indicated by bold lettering and a slash between the two polymorphic possibilities.

FIG. 6. PCR-amplified polymorphic locus of mammalian DNA (SEQ ID NO:14 and SEQ ID NO:15). Shown is a 327 basepair segment of mammalian DNA that was amplified from samples of genomic DNA using the PCR primers TGL240 (SEQ ID NO:7) (biotinylated) and TGL239 (SEQ ID NO:8) (unbiotinylated). Samples of DNA from two homozygous individuals, ESB164 (genotype AA) and EA2014 (genotype BB), were subjected to the analyses described in Example 5. The complete DNA sequence of the A allele at this locus is shown, as SEQ ID NO:14 with the polymorphic sites where the B allele sequence (SEQ ID NO:15) differs from the A allele sequence indicated by the bases underneath the A sequence. The detection primer, TGL308, (SEQ ID NO:9) is shown base-paired with the template strand extending from the biotinylated primer. For the A allele, the first unpaired template base immediately downstream of the 3' end of TGL308 (SEQ ID NO:9) is a C, and for the B allele this base is an A. Thus, the A allele should result in labelling of TGL308 by the ddG mix only, and the B allele should result in labelling by the ddT mix only.

DETAILED DESCRIPTION OF THE INVENTION

Figures 1A, 1B, 1C:
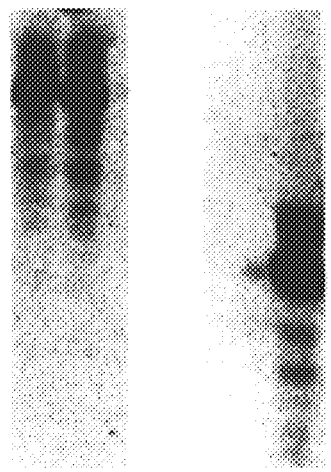
FIGS. 1A–1C. Autoradiography of labeled DNA products after fractionation on a polyacrylamide/urea gel. Panel A shows products of the "A" extension reaction on oligonucleotide primer 182 (SEQ ID NO:1) directed by template oligonucleotides 180 (SEQ ID NO:2) or 181. (SEQ ID NO:3) Panel B shows products of the "B" termination reaction on oligonucleotide primer 182 (SEQ ID NO:1) annealed to template oligonucleotides 180 or 181. Panel C shows the same products as in panel B after purification on magnetic beads. Note: oligodeoxynucleotide 182 was used as supplied by Midland Certified Reagents with no further purification. The minor bands above and below the main band are presumably contaminants due to incomplete reactions or side reactions that occurred during the step-wise synthesis of the oligonucleotide. For a definition of the "A" extension reaction and the "B" termination reaction, see "A. GENERAL METHODS" in the Detailed Description of the Invention.

The subject invention provides a reagent composition comprising an aqueous carrier and an admixture of at least two different terminators of a nucleic acid template-dependent, primer extension reaction. Each of the terminators is capable of specifically terminating the extension reaction in a manner strictly dependent on the identity of the unpaired nucleotide base in the template immediately adjacent to, and downstream of, the 3' end of the primer. In addition, at least one of the terminators is labeled with a detectable marker.

The subject invention further provides a reagent composition comprising an aqueous carrier and an admixture of four different terminators of a nucleic acid template-dependent, primer extension reaction. Each of the terminators is capable of specifically terminating the extension reaction as above and at least one of the terminators is labeled with a detectable marker.

The subject invention further provides a reagent composition comprising an aqueous carrier and an admixture of four different terminators of a nucleic acid template-dependent, primer extension reaction. Each of the terminators is capable of specifically terminating the extension reaction as above and two, three, or four of the terminators are labeled with a different detectable marker.

The subject invention further provides a reagent as described above wherein the terminators comprise nucleotides, nucleotide analogs, dideoxynucleotides, or arabinoside triphosphates. The subject invention also provides a reagent wherein the terminators comprise one or more of dideoxyadenosine triphosphate (ddATP), dideoxycytosine triphosphate (ddCTP), dideoxyguanosine triphosphate (ddGTP), dideoxythymidine triphosphate (ddTTP), or dideoxyuridine triphosphate (ddUTP).

The subject invention further provides a reagent as described above wherein each of the detectable markers attached to the terminators is an isotopically labeled moiety, a chromophore, a fluorophore, a protein moiety, or a moiety to which an isotopically labeled moiety, a chromophore, a fluorophore, or a protein moiety can be attached. The subject invention also provides a reagent wherein each of the different detectable markers is a different fluorophore.

The subject invention also provides a reagent as described above wherein the reagent further comprises pyrophosphatase.

The invented reagent consists of two or more chain terminators with one or more of the chain terminators being identifiably tagged. This reagent can be used in a DNA polymerase primer extension reaction to type nucleic acid sequences of interest that are complementary to one or more oligonucleotide primers by chemically or physically separating the polymerase extended primers from the chain terminator reagent and analyzing the terminal additions. Any kind of terminator that inhibits further elongation can be used, for example, a dideoxynucleoside triphosphate. Several approaches can be used for the labeling and detection of terminators: (1) radioactivity and its detection by either autoradiography or scintillation counting, (2) fluorescence or absorption spectroscopy, (3) mass spectrometry, or (4) enzyme activity, using a protein moiety. The identity of each terminator can be determined individually, i.e., one at a time. In addition, methods which permit independent analyses of each of the terminators permit analysis of incorporation of up to four terminators simultaneously.

The subject invention also provides a method for determining the identity of a nucleotide base at a specific position in a nucleic acid of interest. First, a sample containing the nucleic acid of interest is treated, if such nucleic acid is double-stranded, so as to obtain unpaired nucleotide bases spanning the specific position. If the nucleic acid of interest is single-stranded, this step is not necessary. Second, the sample containing the nucleic acid of interest is contacted with an oligonucleotide primer under hybridizing conditions. The oligonucleotide primer is capable of hybridizing with a stretch of nucleotide bases present in the nucleic acid of interest, immediately adjacent to the nucleotide base to be identified, so as to form a duplex between the primer and the nucleic acid of interest such that the nucleotide base to be identified is the first unpaired base in the template immediately downstream of the 3' end of the primer in the duplex of primer and the nucleic acid of interest. Enzymatic extension of the oligonucleotide primer in the resultant duplex by one nucleotide, catalyzed, for example, by a DNA polymerase, thus depends on correct base pairing of the added nucleotide to the nucleotide base to be identified.

The duplex of primer and the nucleic acid of interest is then contacted with a reagent containing four labeled terminators, each terminator being labeled with a different detectable marker. The duplex of primer and the nucleic acid of interest is contacted with the reagent under conditions permitting base pairing of a complementary terminator present in the reagent with the nucleotide base to be identified and the occurrence of a template-dependent, primer extension reaction so as to incorporate the terminator at the 3' end of the primer.

The net result is that the oligonucleotide primer has been extended by one terminator. Next, the identity of the detectable marker present at the 3' end of the extended primer is determined. The identity of the detectable marker indicates which terminator has base paired to the next base in the nucleic acid of interest. Since the terminator is complementary to the next base in the nucleic acid of interest, the identity of the next base in the nucleic acid of interest is thereby determined.

The subject invention also provides another method for determining the identity of a nucleotide base at a specific position in a nucleic acid of interest. First, a sample containing the nucleic acid of interest is treated, if such nucleic acid is double-stranded, so as to obtain unpaired nucleotide bases spanning the specific position. If the nucleic acid of interest is single-stranded, this step is not necessary. Second, the sample containing the nucleic acid of interest is contacted with an oligonucleotide primer under hybridizing conditions. The oligonucleotide primer is capable of hybridizing with nucleotide bases in the nucleic acid of interest, immediately adjacent to the nucleotide base to be identified, so as to form a duplex between the primer and the nucleic acid of interest such that the nucleotide base to be identified is the first unpaired base in the template immediately downstream of the 3' end of the primer in the duplex of primer and the nucleic acid of interest.

The duplex of primer and the nucleic acid of interest is then contacted with a reagent containing four terminators, only one of the terminators having a detectable marker. The duplex of primer and the nucleic acid of interest is contacted with the reagent under conditions permitting base pairing of a complementary terminator present in the reagent with the nucleotide base to be identified and the occurrence of a template-dependent, primer extension reaction so as to incorporate the terminator at the 3' end of the primer. The net result is that the oligonucleotide primer has been extended by one terminator.

The original duplex of primer and the nucleic acid of interest is then contacted with three different reagents, with a different one of each of the four terminators being labeled in each of the four parallel reaction steps. Next, the products of the four parallel template-dependent, primer extension reactions are examined to determine which of the products has a detectable marker. The product with a detectable marker indicates which terminator has base paired to the next base in the nucleic acid of interest. Since the terminator is complementary to the next base in the nucleic acid of interest, the identity of the next base in the nucleic acid of interest is thereby determined.

Both of the methods for determining the identity of a nucleotide base at a specific position in a nucleic acid of interest label the primer after hybridization between the primer and the template. If the template-dependent enzyme has no exonuclease function, the 3' end of the primer must be base paired for the labeling by a terminator to occur.

The subject invention also provides a method for determining the presence or absence of a particular nucleotide sequence in a sample of nucleic acids. First, the sample of nucleic acids is treated, if such sample of nucleic acids contains double-stranded nucleic acids, so as to obtain single-stranded nucleic acids. If the nucleic acids in the sample are single-stranded, this step is not necessary. Second, the sample of nucleic acids is contacted with an oligonucleotide primer under hybridizing conditions. The oligonucleotide primer is capable of hybridizing with the particular nucleotide sequence, if the particular nucleotide sequence is present, so as to form a duplex between the primer and the particular nucleotide sequence.

The duplex of primer and the particular nucleotide sequence, if any, is then contacted with a reagent containing four labeled terminators, each terminator being labeled with a different detectable marker. The duplex of primer and the particular nucleotide sequence, if any, is contacted with the reagent under conditions permitting base pairing of a complementary terminator present in the reagent with the unpaired template nucleotide base downstream of the 3' end of the primer, the primer being hybridized with the particular nucleotide sequence in the template, and the occurrence of a template-dependent, primer extension reaction so as to incorporate the terminator at the 3' end of the primer. Next, the absence or presence and identity of a detectable marker at the 3' end of the primer are determined. The presence or absence of the detectable marker indicates whether the primer has hybridized to the template. If a detectable marker is absent, the primer did not hybridize to the template, and, therefore, the particular nucleotide sequence is not present in the sample of nucleic acids. If a detectable marker is present, the primer did hybridize to the template, and, therefore, the particular nucleotide sequence is present in the sample of nucleic acids.

The subject invention also provides another method for determining the presence or absence of a particular nucleotide sequence in a sample of nucleic acids. First, the sample of nucleic acids is treated, if such sample of nucleic acids contains double-stranded nucleic acids, so as to obtain single-stranded nucleic acids. Second, the sample of nucleic acids is contacted with an oligonucleotide primer under hybridizing conditions. The oligonucleotide primer is capable of hybridizing with the particular nucleotide sequence, if the particular nucleotide sequence is present, so as to form a duplex between the primer and the particular nucleotide sequence.

The duplex of primer and the particular nucleotide sequence, if any, is then contacted with a reagent containing four terminators, only one of the terminators having a detectable marker. The duplex of primer and the particular nucleotide sequence, if any, is contacted with the reagent under conditions permitting base pairing of a complementary terminator present in the reagent with the unpaired template nucleotide base downstream of the 3' end of the primer, the primer being hybridized with the particular nucleotide sequence in the template, and the occurrence of a template-dependent, primer extension reaction. The net result is the incorporation of the terminator at the 3' end of the primer.

The original duplex of primer and the particular nucleotide sequence, if any, is then contacted with three different reagents, with a different one of each of the four terminators being labeled in each of the four parallel reaction steps. Next, the products of the four parallel, template-dependent, primer extension reactions are examined to determine which, if any, of the products have detectable markers. The absence or presence and identity of the detectable marker indicates whether the primer has hybridized to the template. If no detectable marker is present in any of the products, the primer did not hybridize to the template, and, therefore, the particular nucleotide sequence was not present in the sample of nucleic acids. If a detectable marker is present in any of the products, the primer did hybridize to the template, and, therefore, the particular nucleotide sequence was present in the sample of nucleic acids.

Different versions of the method for determining the identity of a nucleotide base at a specific position in a nucleic acid of interest and the method for determining the presence or absence of a particular nucleotide sequence in a sample of nucleic acids are possible. In the first version, the template is a deoxyribonucleic acid, the primer is an oligodeoxyribonucleotide, oligoribonucleotide, or a copolymer of deoxyribonucleotides and ribonucleotides, and the template-dependent enzyme is a DNA polymerase. This version gives a DNA product. In a second version, the template is a ribonucleic acid, the primer is an oligodeoxyribonucleotide, oligoribonucleotide, or a copolymer of deoxyribonucleotides and ribonucleotides, and the template-dependent enzyme is a reverse transcriptase. This version gives a DNA product. In a third version, the template is a deoxyribonucleic acid, the primer is an oligoribonucleotide, and the enzyme is an RNA polymerase. This version gives an RNA product. In a fourth version, the template is a ribonucleic acid, the primer is an oligoribonucleotide, and the template-dependent enzyme is an RNA replicase. This version gives an RNA product.

Preferably, before the primer extension reaction is performed, the template is capped by the addition of a terminator to the 3' end of the template. The terminator is capable of terminating a template-dependent, primer extension reaction. The template is capped so that no additional labeled terminator will attach at the 3' end of the template. The extension reaction should occur on the primer, not on the template. A dideoxynucleotide can be used as a terminator for capping the template.

Another modification of the method for determining the identity of a nucleotide base at a specific position in a nucleic acid of interest is to separate the primer from the nucleic acid of interest after the extension reaction by using appropriate denaturing conditions. The denaturing conditions can comprise heat, alkali, formamide, urea, glyoxal, enzymes, and combinations thereof. The denaturing conditions can also comprise treatment with 2.0N NaOH.

The nucleic acid of interest can comprise non-natural nucleotide analogs such as deoxyinosine or 7-deaza-2-deoxyguanosine. These analogues destabilize DNA duplexes and could allow a primer annealing and extension reaction to occur in a double-stranded sample without completely separating the strands.

The sample of nucleic acids can be from any source. The sample of nucleic acids can be natural or synthetic (i.e., synthesized enzymatically in vitro). The sample of nucleic acids can comprise deoxyribonucleic acids, ribonucleic acids, or copolymers of deoxyribonucleic acid and ribonucleic acid. The nucleic acid of interest can be a deoxyribonucleic acid, a ribonucleic acid, or a copolymer of deoxyribonucleic acid and ribonucleic acid. The nucleic acid of interest can be synthesized enzymatically in vivo, synthesized enzymatically in vitro, or synthesized non-enzymatically. The sample containing the nucleic acid or acids of interest can comprise genomic DNA from an organism, RNA transcripts thereof, or cDNA prepared from RNA transcripts thereof. The sample containing the nucleic acid or acids of interest can also comprise extragenomic DNA from an organism, RNA transcripts thereof, or cDNA prepared from RNA transcripts thereof. Also, the nucleic acid or acids of interest can be synthesized by the polymerase chain reaction.

The sample can be taken from any organism. Some examples of organisms to which the method of the subject invention is applicable include plants, microorganisms, viruses, birds, vertebrates, invertebrates, mammals, human beings, horses, dogs, cows, cats, pigs, or sheep.

The nucleic acid of interest can comprise one or more moieties that permit affinity separation of the nucleic acid of interest from the unincorporated reagent and/or the primer. The nucleic acid of interest can comprise biotin which permits affinity separation of the nucleic acid of interest from the unincorporated reagent and/or the primer via binding of the biotin to streptavidin which is attached to a solid support. The sequence of the nucleic acid of interest can comprise a DNA sequence that permits affinity separation of the nucleic acid of interest from the unincorporated reagent and/or the primer via base pairing to a complementary sequence present in a nucleic acid attached to a solid support. The nucleic acid of interest can be labeled with a detectable marker; this detectable marker can be different from any detectable marker present in the reagent or attached to the primer.

The oligonucleotide primer can be an oligodeoxyribonucleotide, an oligoribonucleotide, or a copolymer of deoxyribonucleotides and ribonucleotides. The oligonucleotide primer can be either natural or synthetic. The oligonucleotide primer can be synthesized either enzymatically in vivo, enzymatically in vitro, or non-enzymatically in vitro. The oligonucleotide primer can be labeled with a detectable marker; this detectable marker can be different from any detectable marker present in the reagent or attached to the nucleic acid of interest. In addition, the oligonucleotide primer must be capable of hybridizing or annealing with nucleotides present in the nucleic acid of interest, immediately adjacent to, and upstream of, the nucleotide base to be identified. One way to accomplish the desired hybridization is to have the template-dependent primer be substantially complementary or fully complementary to the known base sequence immediately adjacent to the base to be identified.

The oligonucleotide primer can comprise one or more moieties that permit affinity separation of the primer from the unincorporated reagent and/or the nucleic acid of interest. The oligonucleotide primer can comprise biotin which permits affinity separation of the primer from the unincorporated reagent and/or nucleic acid of interest via binding of the biotin to streptavidin which is attached to a solid support. The sequence of the oligonucleotide primer can comprise a DNA sequence that permits affinity separation of the primer from the unincorporated reagent and/or the nucleic acid of interest via base pairing to a complementary sequence present in a nucleic acid attached to a solid support.

The subject invention also provides a method of typing a sample of nucleic acids which comprises identifying the base or bases present at each of one or more specific positions, each such nucleotide base being identified using one of the methods for determining the identity of a nucleotide base at a specific position in a nucleic acid of interest as outlined above. Each specific position in the nucleic acid of interest is determined using a different primer. The identity of each nucleotide base or bases at each position can be determined individually or the identities of the nucleotide bases at different positions can be determined simultaneously.

The subject invention also provides another method of typing a sample of nucleic acids which comprises determining the presence or absence of one or more particular nucleotide sequences, the presence or absence of each such nucleotide sequence being determined using one of the methods for determining the presence or absence of a particular nucleotide sequence in a sample of nucleic acids as outlined above.

The subject invention also provides an additional method of typing a sample containing nucleic acids. First, the presence or absence of one or more particular nucleotide sequences is determined; the presence or absence of each such nucleotide sequence is determined using one of the methods for determining the presence or absence of a particular nucleotide sequence in a sample of nucleic acids as outlined above. Second, the nucleotide base or bases present at each of one or more specific positions is identified; each such base is identified using one of the methods for determining the identity of a nucleotide base at a specific position in a nucleic acid of interest as outlined above.

The subject invention further provides a method for identifying different alleles in a sample containing nucleic acids which comprises identifying the base or bases present at each of one or more specific positions. The identity of each nucleotide base is determined by the method for determining the identity of a nucleotide base at a specific position in a nucleic acid of interest as outlined above.

The subject invention also provides a method for determining the genotype of an organism at one or more particular genetic loci which comprises obtaining from the organism a sample containing genomic DNA and identifying the nucleotide base or bases present at each of one or more specific positions in nucleic acids of interest. The identity of each such base is determined by using one of the methods for determining the identity of a nucleotide base at a specific position in a nucleic acid of interest as outlined above. The identity of the nucleotide bases determine the different alleles and, thereby, determine the genotype of the organism at one or more particular genetic loci.

The chain termination reagent in combination with an appropriate oligonucleotide primer, and a DNA polymerase with or without an associated 3' to 5' exonuclease function, and an appropriate salt and cofactor mixture, can be used under appropriate hybridization conditions as a kit for diagnosing or typing nucleic acids, if appropriate primer separation techniques are used. To simplify the primer separation and the terminal nucleotide addition analysis this invention makes use of oligonucleotides that are modified in such ways that permit affinity separation as well as polymerase extension. The 5' termini and internal nucleotides of synthetic oligonucleotides can be modified in a number of different ways to permit different affinity separation approaches, e.g., biotinylation. These affinity reagents can be used with the terminator mixture to facilitate the analysis of extended oligonucleotide(s) in two ways:

(1) If a single affinity group is used on the oligonucleotide (s), the oligonucleotide(s) can be separated from the unincorporated terminator reagent. This eliminates the need of physical or size separation.

(2) More than one oligonucleotide can be separated from the terminator reagent and analyzed simultaneously if more than one affinity group is used. This permits the analysis of several nucleic acid species or more nucleic acid sequence information per extension reaction.

The affinity group(s) need not be on the priming oligonucleotide but could, alternatively, be present on the template. As long as the primer remains hydrogen bonded to the template during the affinity separation step, this will allow efficient separation of the primer from unincorporated terminator reagent. This also has the additional benefit of leaving sites free on the primer for the convenient attachment of additional moieties. For example, the 5'-terminus of the primer could be modified by coupling it to a suitable fluorescent group such as rhodamine, allowing the amount of primer in the primer:template complex to be easily quantified after the affinity separation step. The amounts of 3'-terminating terminators could then be normalized to the total amount of annealed primer.

The oligonucleotide primers and template can be any length or sequence, can be DNA or RNA, or any modification thereof. It is necessary, however, that conditions are chosen to optimize stringent hybridization of the primers to the target sequences of interest.

The conditions for the occurence of the template-dependent, primer extension reaction can be created, in part, by the presence of a suitable template-dependent enzyme. Some of the suitable template-dependent enzymes are DNA polymerases. The DNA polymerase can be of several types. The DNA polymerase must, however, be primer and template dependent. For example, *E. coli* DNA polymerase I or the "Klenow fragment" thereof, T4 DNA polymerase, T7 DNA polymerase ("Sequenase"), *T. acuaticus* DNA polymerase, or a retroviral reverse transcriptase can be used. RNA polymerases such as T3 or T7 RNA polymerase could also be used in some protocols. Depending upon the polymerase, different conditions must be used, and different temperatures ranges may be required for the hybridization and extension reactions.

The reagents of the subject invention permit the typing of nucleic acids of interest by facilitating the analysis of the 3' terminal addition of terminators to a specific primer or primers under specific hybridization and polymerase chain extension conditions. Using only the terminator mixture as the nucleoside triphosphate substrate ensures addition of only one nucleotide residue to the 3' terminus of the primer in the polymerase reaction. Using all four terminators simultaneously ensures fidelity, i.e., suppression of misreading.

By specifically labeling one or more of the terminators, the sequence of the extended primer can be deduced. In principle, more than one reaction product can be analyzed per reaction if more than one terminator is specifically labeled.

By specifically tagging the oligonucleotide primer(s), or template(s) with a moiety that does not affect the 3' extension reaction yet permits affinity separation, the extension product(s) can be separated post-reaction from the unincorporated terminators, other components of the reagents, and/or the template strand. Several oligonucleotides can be analyzed per extension reaction if more than one affinity agent is used.

In principle, the combination of four differently labeled terminators and many primers or templates tagged with different groups permits the typing of many different nucleic acid sequences simultaneously.

Specificity in this diagnostic reaction is determined by (1) the stringency of oligonucleotide hybridization and (2) the sequence information gained by the single residue extension.

A. General Methods

1. Biotinylation of oligodeoxynucleotides.

Oligodeoxynucleotides, terminated at their 5'-ends with a primary amino group, were ordered from Midland Certified Reagents, Midland, Tex. These were biotinylated using biotin-XX-NHS ester (Clontech Laboratories, Inc., Palo Alto, Calif.), a derivative of biotin-N-hydroxysuccinimide. Reagents used were from the Clontech biotinylation kit. Typically, the oligonucleotide (9 nanomoles) was dissolved in 100 $\mu$l of 0.1M NaHCO/Na$_2$CO$_3$ (pH 9), and 25 $\mu$l of N,N-dimethylformamide containing 2.5 mg biotin-XX-NHS-ester was added. The mixture was incubated overnight at room temperature. It was then passed over a 6 ml Sephadex G-25 column ("DNA grade"—Pharmacia) equilibrated with H$_2$O. Eluate fractions containing DNA were identified by mixing 4 $\mu$l aliquots with an equal volume of ethidium bromide (2 $\mu$g/ml) and the DNA-induced fluorescence was monitored with a UV transilluminator. Unreacted ester was detected by UV absorption at 220 nm. The tubes containing DNA were pooled, concentrated in a Centricon-3 microconcentrator (Amicon), and passed over Sephadex again.

Inhibition of the binding of [$^3$H]-biotin to magnetic M-280 streptavidin Dynabeads (Dynal) was used to assay quantitatively the extent of biotinylation of the oligonucleotides. Eppendorf tubes and pipet tips were siliconized. A known amount (5–10 pmoles) of biotin-labeled oligonucleotide in 10 $\mu$l 0.1M NaCl was added to tubes containing 25 $\mu$l of 1:4 suspension of beads in 0.1M NaCl. The tubes were rotated for one hour on a Labquake shaker (Labindustries, Inc.). Increasing amounts of [$^3$H]-biotin (5–35 pmoles) in 20 $\mu$l of 0.1M NaCl were added to the tubes and these were rotated again for one hour. Tubes were put on a Dynal MPC-E magnet to remove the beads from suspension, 10 $\mu$l aliquots of the supernatant were withdrawn, and the amount of radioactivity in these was measured using a Beckman LS 5000 TD liquid scintillation counter. Counts were compared to those from tubes to which no oligonucleotide had been added. Alternatively, for some primers, biotinylation was monitored by size fractionation of the reaction products using analytical polyacrylamide gel electrophoresis in the presence of 8M urea.

2. Template-dependent primer extension/termination reactions.

Approximately five pmoles of 5'-biotinylated oligodeoxynucleotide template (see above) were mixed with approximately three pmoles of primer in 1X sequencing buffer (from Sequenase Version 2.0 kit, US Biochemical Corp.) (10 $\mu$l final volume), the mixture was incubated at 65° C. for 2 min, then allowed to cool to room temperature in order to anneal the primer and template. The solution containing the annealed template-primer was separated into two 5 $\mu$l portions, A and B, to which were added the following: Reactions A (for normalizing template concentrations)—0.5 $\mu$l of 100 mM dithiothreitol, 1 $\mu$l each of 10 $\mu$M DATP, dGTP, ddCTP, 0.5 $\mu$l of "Mn buffer" (from Sequenase Version 2.0 kit, US Biochemical Corp.), 0.5 $\mu$l of [$^{35}$S]-$\alpha$-thio-dTTP (10 mCi/ml, 1180 Ci/mmole) (Dupont-NEN), 1 $\mu$l of Sequenase (1:8 dilution, US Biochemical Corp.); Reactions B (for template-specific labeling of primer 3'-ends)—same additions as in Reactions A except the nucleotides used were ddCTP, ddGTP, ddTTP, and [$^{35}$S]-$\alpha$-thio-ddATP. Reactions were for 5 min at 37° C. Control reactions omitting the primer or the Sequenase were also performed. Aliquots were removed and analyzed by electrophoresis on a 15% polyacrylamide, 8 M urea, DNA sequencing gel (see Maniatis, T., et al., *Molecular Cloning. a Laboratory Manual,* Cold Spring Harbor Laboratory (1982)). The gel was fixed in 10% methanol, 10% acetic acid, dried down onto Whatman's 3MM paper, and exposed to Kodak X-Omat AR film. Alternatively, for purposes of analyzing the products by liquid scintillation counting, the biotinylated template or template-primer was bound to an excess of M-280 streptavidin Dynabeads (Dynal) before or after the Sequenase reaction (see above, "1. Biotinylation of oligodeoxynucleotides", for binding conditions). Beads were washed three times with 0.1M NaCl to remove unincorporated label, then scintillation fluid was added and the radioactivity measured by liquid scintillation counting.

3. Generation of templates from polymerase chain reaction products

Polymerase chain reaction (PCR) reactions were carried out where one or the other of the amplification primers flanking the target stretch of DNA were biotinylated as described above. These primers (2 $\mu$mol final concentration) and the target DNA (up to 1 $\mu$g) were incubated with 2.5 units of Taq polymerase (Perkin Elmer/Cetus), 200 $\mu$M each of DATP, dCTP, dGTP, and dTTP, 10 mM Tris-HCl (pH 8.3), 50 mM KCl, 1.5 mM MgCl$_2$, and 0.01% gelatin (Sigma). Reaction mixtures were overlayed with paraffin oil and incubated for 30 cycles in Perkin Elmer/Cetus thermocycler. Each cycle consisted of 1 min at 94° C., 2 min at 60° C., and 3 min at 72° C. Reaction products were purified by phenol/chloroform extraction and ethanol precipitation, then analyzed by ethidium bromide staining after electrophoresis on a polyacrylamide gel. The yield of duplex PCR product was typically about 10 $\mu$g.

Approximately 5 $\mu$g of this PCR product was incubated with gentle agitation for 60 min with 50 $\mu$L of a suspension of prewashed M-280 Dynabeads in 0.1M NaCl. The beads with the bound DNA (approximately 15 pmoles) were then incubated for 5 min at 25° C. with 0.15M NaOH. Beads were washed once with 0.15M NaOH to remove the unbiotinylated DNA strand, then washed three times with $H_2O$. The beads were resuspended in $H_2O$ and the strand bound to the beads via the biotin-streptavidin link was used as template for further primer extension reactions.

B. Examples

Example 1

| Primer oligo 182: | 5' GCCTTGGCGTTGTAGAA 3' |
| Template oligos 180(C)/181(T): | 3' TCGGGTCGGAACCGCAACATCTT$^C$/TATAGACTA 5' |

Oligonucleotides 180 (SEQ ID NO:2) and 181 (SEQ ID NO:3) were synthesized with primary amino groups attached to their 5' termini. These were coupled with biotin as described above. Oligonucleotide 182 (SEQ ID NO:4) was annealed as a primer and extension reactions "A" and "B" (see above) were carried out. The expected template-dependent 3'-terminal extensions to oligonucleotide 182 (SEQ ID NO:1) were as follows ("*" preceding a nucleotide signifies a radioactive label):

| Template | Reaction A | Reaction B |
|---|---|---|
| 180 | dG-*dT-dk-*dT-ddC | -ddG |
| 181 | dA-*dT-dA-*dT-ddC | -*ddA |

Thus, in the "A" reactions, both template oligonucleotides will direct a radioactively-labelled five nucleotide extension of the primer; the amount of labeling should be proportional to the amount of productively primed template present in the reactions. In the "B" reactions, both templates will direct a one nucleotide extension of the primer, but only for template 181 (SEQ ID NO:3) should this result in labeling of the primer. The "B" reaction, therefore, is an example of template-directed, sequence-specific labeling of an oligonucleotide via DNA polymerase-catalyzed extension of a productive primer-template complex.

The reaction products were fractionated by size on a 15% polyacrylamide/8M urea sequencing gel and visualized by autoradiography. The results (FIG. 1) show that, as expected, the "A" reactions yield labeling and extension of both primers whereas the "B" reaction results in labeling that is strongly biased in favor of template 181 (SEQ ID NO:3). Panel C in FIG. 1 shows a gel analysis of the same reaction products as in Panel B, except the reaction products were first purified as described above using M-280 streptavidin Dynabeads.

Example 2

The experiment described in Example 1 shows template-directed labeling of oligonucleotide primer 182 (SEQ ID NO:4) in which the labeling is specific with respect to oligonucleotides or other species that migrate similarly on a polyacrylamide gel. In order to assess more generally the template-directed specific labeling of oligonucleotide 182 (SEQ ID NO:1) with respect to all other labeled species, regardless of gel mobility, a direct measurement of incorporated radioactivity was performed. In this experiment, both reactions "A" and "B" were performed, reaction products were purified using Dynabeads, and total radioactivity in the aliquots was measured by liquid scintillation counting. This procedure assesses both misincorporation of label into other species and, in addition, the efficiency of the Dynabead washing procedure with respect to unincorporated nucleotides. As a practical matter, it would be of interest to minimize both sources of non-specific label in order to have a simple, non-gel-based, procedure for assessing specific, template-directed labeling of the primer. The results of directly counting the reaction products after washing on the magnetic beads are as follows (all results expressed as cpm of $^{35}S$):

| Reaction | Template 180 | Template 181 |
|---|---|---|
| A, complete | 325,782 | 441,823 |
| A, no polymerase | 5,187 | 5,416 |
| A, no primer | 4,351 | 12,386 |
| B, complete | 5,674 | 176,291 |
| B, no polymerase | 2,988 | 1,419 |
| B, no primer | 1,889 | 1,266 |

As can be seen from these results, specific template-directed labeling of primer 182 (SEQ ID NO:1) can also be determined by measuring the total radioactivity of the reaction products after washing with magnetic beads to remove unreacted nucleotides. The background in this experiment due to nonspecific label from all other sources was approximately 3–4% (compare templates 180 (SEQ ID NO:2) and 181 (SEQ ID NO:30 in the "B, complete" reaction). Control experiments ("no polymerase" and "no primer") showed that the bulk of the background label was probably contributed by unincorporated nucleotides that were not completely removed by the washing step. The "A, complete" reactions showed that, for both templates, productive template:primer complexes were present.

Example 3

Two amplification primers, TGL 105 (SEQ ID NO:10) and TGL 106 (SEQ ID NO:11) (FIG. 2), were used to amplify a cloned stretch of bovine DNA (SEQ ID NO:13) containing two DNA sequence polymorphisms: a C or T at position 114 and an A or G at position 190 (FIG. 2). DNAs containing these polymorphisms were molecularly cloned and available on plasmids, as follows: plasmid p183, C114 and A190; plasmid p624, T114 and A190; plasmid p814, C114 and G190. Four PCR reactions with biotinylated primers were performed to amplify and purify specific strands of these plasmids for use as templates:

| Primers | Plasmids | Detection Primers |
|---|---|---|
| 105 biotinylated, 106 unbiotinylated | p183 and p624 | TGL 182 (SEQ ID NO: 1) |
| 105 unbiotinylated, 106 biotinylated | p183 and p814 | TGL 166 (SEQ ID NO: 12) |

The duplex PCR products were bound to magnetic microspheres, denatured with NaOH, and the biotinylated strand purified as described above. Templates prepared with biotinylated TGL 105 (SEQ ID NO:10) were subjected to analysis by DNA sequencing with unbiotinylated primer TGL 106 (SEQ ID NO:11) in order to measure the amount of template present. Similarly, template prepared using biotinylated TGL 106 (SEQ ID NO:11) was analyzed by sequencing with unbiotinylated TGL 105 (SEQ ID NO:10).

Approximately equal amounts of template (2 pmoles) were annealed for 5 min at 65° C to the polymorphism detection primers, TGL 182 (SEQ ID NO:1) and TGL 166

Figure 3:
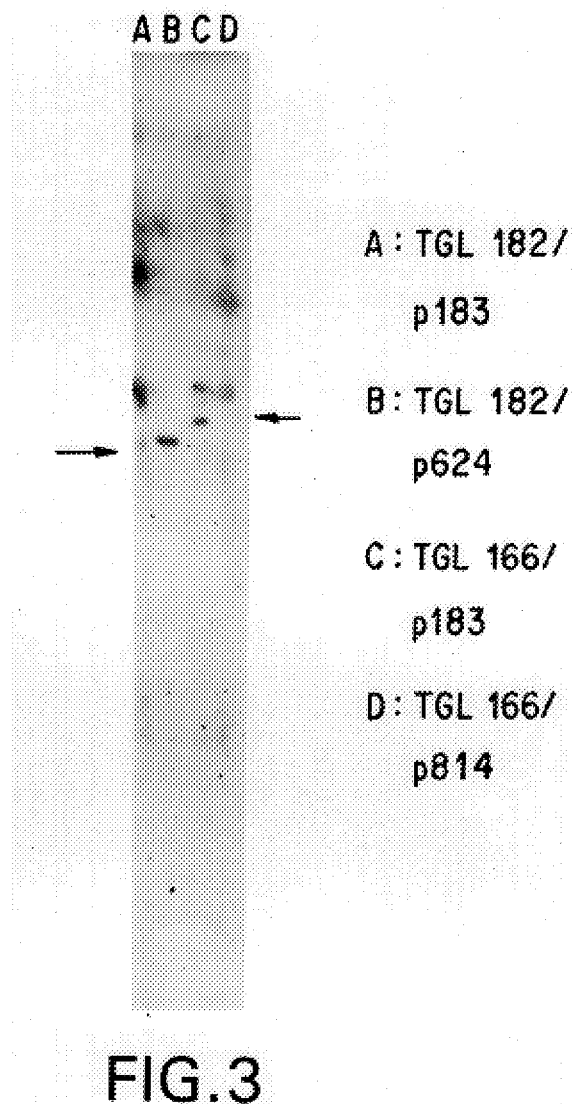
FIG. 3. Autoradiogram of gel-analyzed polymorphism test on PCR products. Templates from PCR products of p183, p624, or p814 were analyzed with the detection primers, TGL182 (SQ ID NO:1) and TGL166, (SEQ ID NO:12) in a template-directed chain extension experiment, as described in the specification. Reaction products were fractionated by size on a polyacrylamide/urea DNA sequencing gel, and incorporation of [$^{35}$S]-α-thio-dideoxy adenosine monophosphate was assayed by autoradiography.

(SEQ ID NO:12) (see above and FIG. 2). These primers hydrogen-bond to the templates in a sequence-specific fashion such that their 3'-termini are adjacent to nucleotide positions 114 and 190, respectively (FIG. 2 and SEQ ID NO:13). Template-directed primer extension reactions (reaction "B" conditions) were carried out on these primer-:template complexes in the presence of the four ddNTPs, one of which (ddATP) was labeled. The products of these extension reactions were analyzed by electrophoresis on a 15% polyacrylamide/8M urea gel followed by autoradiography (FIG. 3).

Example 4

| | |
|---|---|
| Primer oligo TGL391: | 5'TGTTTTGCACAAAAGCA3' (SEQ ID NO: 4) |
| Primer oligo TGL346: | 5'GTTTTGCACAAAAGCAT3' (SEQ ID NO: 5) |
| Template oligo TGL382: | 3'CACAAAACGTGTTTTCGTAGGA5'-biotin: (streptavidin-bead) (SEQ ID NO: 6) |

Oligonucleotide TGL382 (SEQ ID NO:6) was purchased from the Midland Certified Reagent Company, Midland, Tex. It was biotinylated using Midland Certified Reagent Company's "Biotin dX" reagent (a biotin derivative phosphoramidite) which is suitable for use in automated DNA synthesis in the 5' terminal nucleotide position. The biotinylated oligonucleotide was then purified by anion exchange HPLC. Streptavidin-conjugated M-280 Dynabeads were washed in TNET buffer (10 mM Tris-HCl, pH 7.5, 100 mM NaCl, 1 mM EDTA, 0.1% Triton X-100) and resuspended in the same buffer at a concentration of $7 \times 10^8$ beads/ml. 10–100 pmoles of biotinylated oligonucleotide TGL382 (SEQ ID NO:6) was incubated with 100 $\mu$l of the Dynabead suspension in TNET for 30 minutes at 20° C. in order to allow the biotin moiety to bind to the streptavidin. The beads were then washed (using a magnet to immobilize them) three times with 200 $\mu$l of TNET and resuspended in 100 $\mu$l of TNET. For annealing, 25 $\mu$l of this suspension of the Dynabeads with the attached template oligonucleotide was immobilized with the magnet, the TNET withdrawn, and 25 $\mu$l of 40 mM Tris-HCL, pH 7.5, 20 mM MgCl$_2$, 50 mM NaCl, containing 2 $\mu$M of oligonucleotide primers 346 or 391, was added. The template and each primer were annealled by incubating them for 5 minutes at 65° C., followed by slow cooling over a period of 20 minutes to room temperature. Beads containing the bound template-primer complexes were washed twice with 200 $\mu$l TNET, followed by resuspension in 25 $\mu$l of 40 mM Tris-HCl, pH 7.5, 20 mM MgCl$_2$, 50 mM NaCl.

The following ddNTP mixes were used:

| $^{35}$S-labelled dideoxynucleoside triphosphate mixes (labelled nucleotide indicated in the form ddN*TP): | | | |
|---|---|---|---|
| ddG Mix: | 5 $\mu$M ddG*TP 10 $\mu$M ddCTP | 10 $\mu$M ddATP | 10 $\mu$M ddTTP |
| ddA Mix: | 10 $\mu$M ddGTP 10 $\mu$M ddCTP | 5 $\mu$M ddA*TP | 10 $\mu$M ddTTP |
| ddT Mix: | 10 $\mu$M ddGTP 10 $\mu$M ddCTP | 10 $\mu$M ddATP | 5 $\mu$M ddT*TP |
| ddC Mix: | 10 $\mu$M ddGTP 5 $\mu$M ddC*TP | 10 $\mu$M ddATP | 10 $\mu$M ddTTP |

The ddN*TPs were the four respective [α-thio-$^{35}$S] dideoxynucleoside triphosphates (purchased from New England Nuclear).

For each bead-bound, template-primer complex, four extension reactions were carried out, one reaction for each of the four ddNTP mixes. Extension reactions contained the following components: 5.0 $\mu$l bead suspension containing the annealled template-primer complex, 0.5 $\mu$l of 100 mM dithiothreitol, 0.5 $\mu$l of "Mn$^{++}$ solution" (100 mM MnCl$_2$, 150 mM DL-isocitrate, pH 7.0; purchased from U.S. Biochemicals, Cleveland, Ohio), 1.0 $\mu$l of ddG, ddA, ddT, or ddC mix, 2.0 $\mu$l of H$_2$O, and 1.0 $\mu$l of T7 DNA polymerase ("Sequenase", version 2.0, US Biochemicals, 1625 units/ml in 50 mM Tris-HCl, pH 7.5, 10 mM 2-mercaptoethanol, 1 mg/ml bovine serum albumin).

Reactions were allowed to proceed for 15 minutes at 20° C., then stopped by washing the magnetically immobilized beads three times with 500 $\mu$l TNET. Beads were resuspended in final volume of 25 $\mu$l TNET prior to the detection assays.

Incorporation of labelled dideoxynucleotides by the primer extension reaction was assayed two different ways: gel electrophoresis followed by autoradiography, and direct autoradiographic analysis of labelled DNA.

Figure 4:
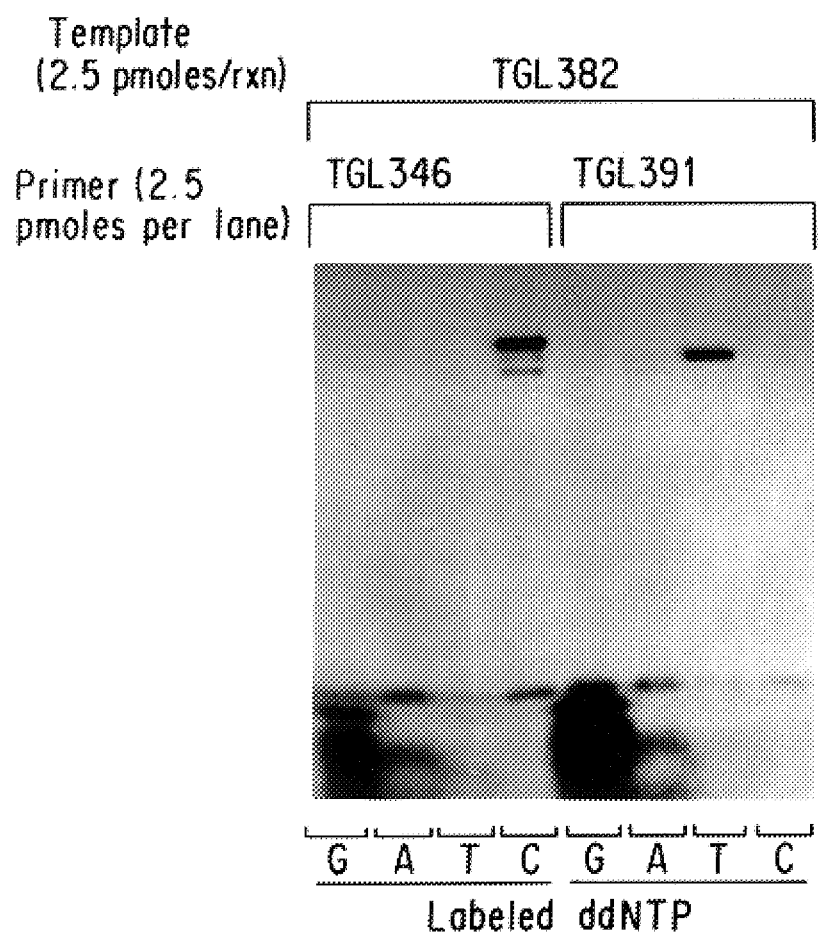
FIG. 4. Gel electrophoretic analysis of the labelled extension products of primers TGL346 (SEQ ID NO:5) and TGL391 (SEQ ID NO:4). Productive primer-template complexes of TGL346 or TGL391 with the bead-bound oligonucleotide template, TGL382, (SEQ ID NO:6) were subjected to primer extension labelling reactions with the four different [α-thio-$^{35}$S]dideoxynucleoside triphosphate mixes. Labelled primer DNA was released from the washed beads and electrophoresed on an 8% polyacrylamide/8M urea DNA sequencing gel (2.5 pmoles of primer/lane), then analyzed by autoradiography. The four lanes shown for the primer TGL346 indicate that labelling occurred predominantly with the ddC mix, indicating that the next unpaired base in the TGL382 template adjacent to the 3' end of TGL346 was a G (see sequence given in Example 4). The four lanes shown for the primer TGL391 indicate that the labelling occurred predominantly with the ddT mix, indicating that the next unpaired base in the TGL382 template adjacent to the 3' end of TGL391 was an A.

1. Gel electrophoresis followed by autoradiography ($^{35}$S-labelled material only). Samples of washed, bead-bound DNA were heated at 94° C. for 5 minutes in 10 $\mu$l of formamide loading buffer (80% formamide, 10 mM Tris-HCl, pH 8, 1 mM EDTA, 0.02% bromphenol blue) to denature the DNA and release the labelled primer from the primer:template complex. Samples were analyzed by electrophoresis on 8 or 12.5% polyacrylamide/8M urea sequencing gels (19:1 acrylamide:bis-acrylamide ratio; 100 mM Tris-HCl, 100 mM borate, 2 mM EDTA, pH 8.3, running buffer; 60 watts constant power). After electrophoresis, gels were either dried down onto filter paper or frozen at −80° C. to prevent diffusion, covered with plastic wrap, and exposed to X-ray film to visualize the labelled DNA by autoradiography (FIG. 4).

Figure 5:
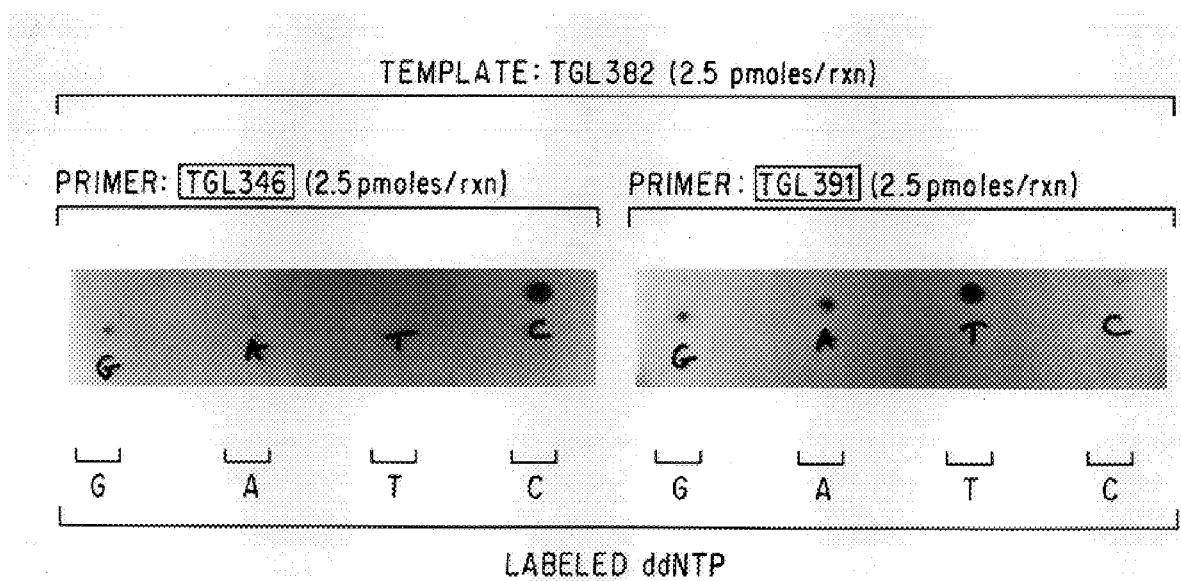
FIG. 5. Autoradiographic analyses of total radioactivity bound to beads. The bead suspensions, containing the products of the extension reactions described in FIG. 5, were spotted onto filter paper (1 pmole of primer per spot) and exposed to X-ray film to assay total bead-bound radioactivity. As shown, TGL346 (SEQ ID NO:5) predominantly incorporated label from the ddC mix and TGL391 (SEQ ID NO:4) predominantly from the ddT mix.

2. Direct autoradiographic analysis of labelled DNA. For the analysis of total radioactivity bound to the beads, 10 $\mu$l aliquots of the bead suspensions in TNET were spotted directly onto filter paper or nylon membranes. Filters or membranes were dried under an incandescent lamp, covered with plastic wrap, and exposed to X-ray film (FIG. 5).

Example 5

| | |
|---|---|
| TGL240: | 5'AGATGATGCTTTTGTGCAAAACAC3' (SEQ ID NO: 7) |
| TGL239: | 5'TCAATACCTGAGTCCCGACACCCTG3' (SEQ ID NO: 8) |
| TGL308: | 5'AGCCTCAGACCGCGTGGTGCCTGGT3' (SEQ ID NO: 9) |

Oligonucleotide TGL240 (SEQ ID NO:2) was synthesized with a primary amino group attached to its 5' terminus and coupled with biotin as described above. TGL240 (biotinylated) and TGL239 (SEQ ID NO:8) (unbiotinylated) were used to amplify, via the polymerase chain reaction procedure (see "A. General Methods"), a region of DNA comprising a particular genetic locus in samples of mammalian genomic DNA. DNAs from two different individuals, each homozygous for a particular set of linked sequence polymorphisms (the "A" allele and the "B" allele—see FIG. 6 and SEQ ID NO:14 and SEQ ID NO:15), were examined. After the PCR reaction, 2–20 pmoles of duplex PCR DNA was incubated with 100 $\mu$l of streptavidin-conjugated M-280 Dynabeads ($7 \times 10^8$ beads/ml) in TNET buffer in order to bind the biotinylated strand to the beads. After binding, the beads were magnetically immobilized and washed three times with 200 μl of TNET, then resuspended in 100 μl of TNET. To remove the non-biotinylated strand, 500 μl of 0.15N NaOH was added and the suspension incubated for 30 minutes at 20° C. The beads were then magnetically immobilized and washed once with 250 μl of 0.15N NaOH, three times with 500 μl TNET, and resuspended in 100 μl of TNET.

Figure 7:
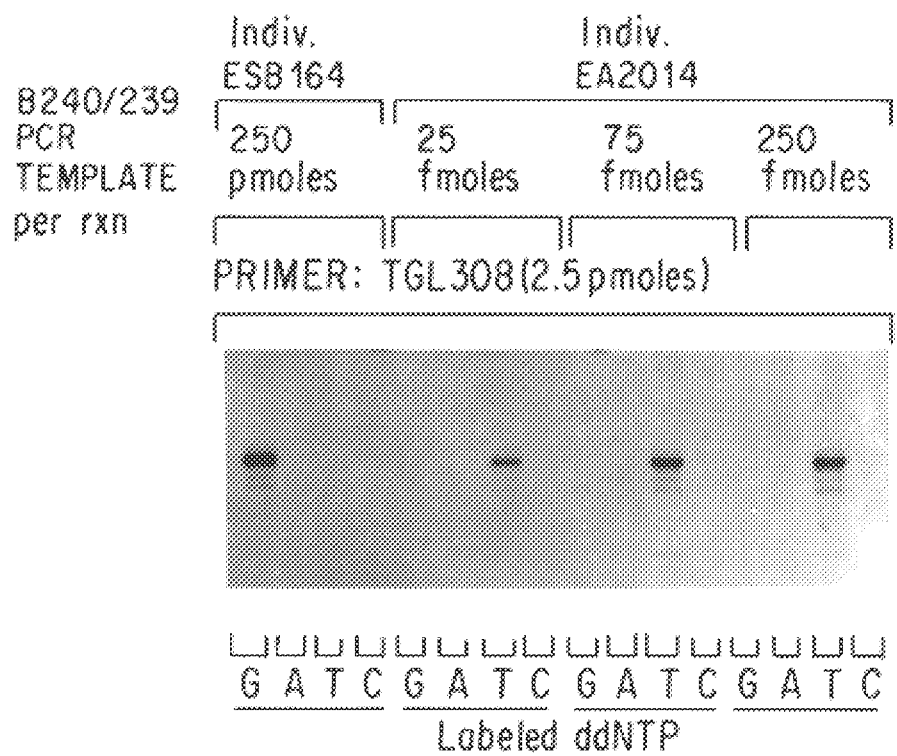
FIG. 7. Gel electrophoretic analysis of PCR products from two different homozygous individuals. Primers TGL240 (SEQ ID NO:7) and TGL239 (SEQ ID NO:8) were used to amplify genomic DNA (obtained from blood) from two individuals, ESB164 and EA2014. The products of the extension reactions for primer TGL308, (SEQ ID NO:19) annealed to the bead-bound, PCR-generated template as outlined in FIG. 7, were analyzed by electrophoresis on an 8% polyacrylamide/8 M urea DNA sequencing gel as outlined in FIG. 5. Shown for individual ESB164 (genotype AA: labelling expected from the ddG mix) are 250 fmoles of extended primer from the four different ddNTP labelling reactions. Shown for individual EA2014 (genotype BB: labelling expected from the ddT mix) are loadings of 25, 75, and 250 fmoles of extended primer from the four different ddNTP labelling reactions.
Figure 8:
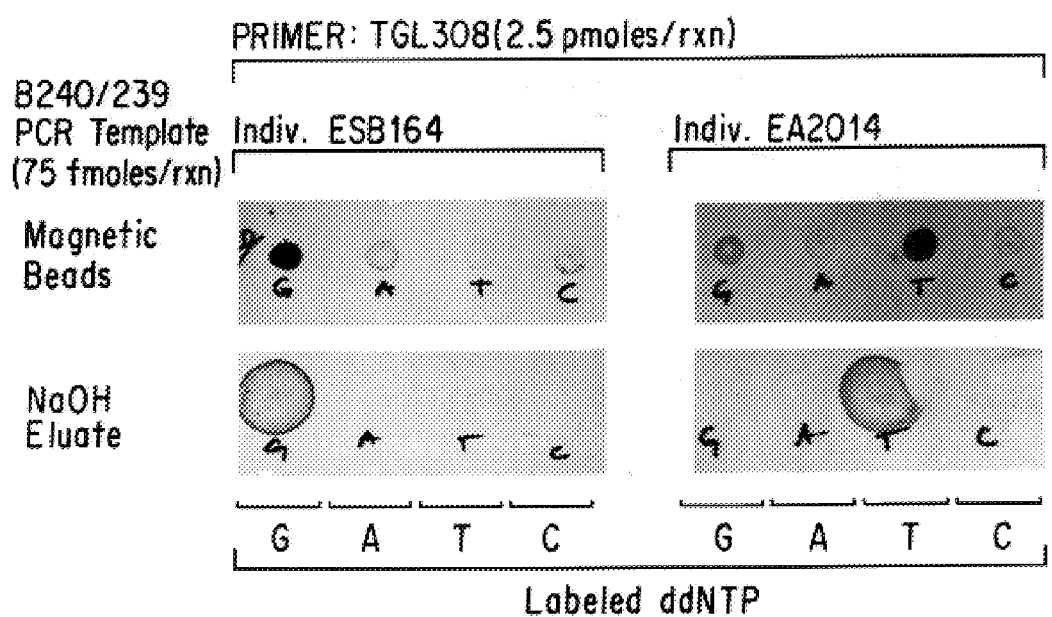
FIG. 8. Autoradiographic analyses of total and NaOH-eluted radioactivity from TGL308 (SEQ ID NO:9) primer extension reactions. Primer TGL308 was used to analyze the genotypes of individuals ESB164 and EA2014 as outlined in Example 5 and FIGS. 7 and 8. Total bead-associated radioactivity was determined by directly spotting a suspension of beads containing 75 fmoles of primer onto filter paper followed by autoradiographic detection of the label in the spot. Radioactivity specifically associated with the TGL308 primer (SEQ ID NO:9) was determined by magnetically immobilizing the beads, eluting the primer with NaOH as described in Examples 4 and 5, and spotting on filter paper an amount corresponding to 75 fmoles. Label in these spots was also detected by autoradiography.

The detection primer, oligonucleotide TGL308 (SEQ ID NO:9) (FIG. 6), was annealled to the bead-bound PCR-generated template as described above in Example 4. Further washes, extension reactions, and detection assays were also carried out as described in Example 4. A gel autoradiographic analysis of the labelled primer extension products for the two homozygous individuals, ESB164 ("AA" genotype) and EA2014 ("BB" genotype), is shown in FIG. 7. Autoradiographic analyses of total bead-bound radioactivity, or primer-associated radioactivity after NaOH elution, are shown for these same individuals using the filter spotting assay (FIG. 8). For the analysis of primer only, 10 μl of 0.4N NaOH was added to 10 μl of the bead suspension. After incubation for 10 minutes at room temperature, the beads were immobilized magnetically and the supernatant withdrawn and spotted onto nylon blotting membrane.

C. Preferred Embodiment

A particularly advantageous way to practice the present invention involves obtaining from a convenient source, such as blood, epithelium, hair, or other tissue, samples of DNA or RNA, then amplifying in vitro specific regions of the nucleic acid using the polymerase chain reaction, transcription-based amplification (see Kwoh, et al., Proc. Natl. Acad. Sci. 80:1173 (1989)), etc. Amplification is accomplished using specific primers flanking the region of interest, with one or more of the primers being modified by having an attached affinity group (although in any given reaction only one such primer is modified at a time). A preferred modification is attachment of biotin moieties to the 5'-termini of the primers. A sample (typically, 0.5–5 pmoles) of the amplified DNA is then bound to streptavidin-conjugated magnetic microspheres (e.g., Dynal M-280 "Dynabeads") via the attached biotin moiety on the amplification primer. The DNA is denatured by adjusting the aqueous suspension containing the microspheres to a sufficiently alkaline pH, and the strand bound to the microspheres via the biotin-streptavidin link is separated from the complementary strand by washing under similar alkaline conditions. To accomplish this, the microspheres are centrifuged or immobilized by the application of a magnetic field. The microsphere-bound strand is then used as a template in the remaining manipulations.

To the template strand, generated as described above, a specific primer oligonucleotide is bound under high stringency annealing conditions, the sequence of the primer being consistent with unique binding to a site on the template strand immediately adjacent to a known DNA sequence polymorphism. A preferred sequence and mode of binding for the primer ensures that the primer forms a duplex with the template such that the 3'-terminal nucleotide of the primer forms a Watson-Crick basepair with the template nucleotide immediately adjacent to the site of the first nucleotide in the sequence polymorphism, without the duplex overlapping any of the polymorphic sequence to be analyzed. This arrangement causes the nucleotides added via template-directed, DNA polymerase-catalyzed, extension of the primer to be determined unambiguously by the polymorphic nucleotide sequence in the template.

The above-described primer:template complex is contacted, under conditions of salt, pH, and temperature compatible with template-directed DNA synthesis, with a suitable DNA polymerase and four different chain-terminating nucleotide analogues known to form specific base pairs with the bases in the template. Most likely, but not necessarily, the bases in the template as well as the chain-terminating analogues are based on the common nucleosides: adenosine, cytosine, guanine or inosine, thymidine or uridine. A preferred set of chain-terminating analogues are the four dideoxynucleoside triphosphates, ddATP, ddCTP, ddGTP, and ddTTP, where each of the four ddNTPs has been modified by attachment of a different fluorescent reporter group. These fluorescent tags would have the property of having spectroscopically distinguishable emission spectra, and in no case would the dideoxynucleoside triphosphate modification render the chain-terminating analogue unsuitable for DNA polymerase-catalyzed incorporation onto primer 3'-termini. The result of DNA polymerase-catalyzed chain extension in such a mixture with such a primer:template complex is the quantitative, specific and unambiguous incorporation of a fluorescent chain-terminating analogue onto the 3'-terminus of the primer, the particular fluorescent nucleotide added being solely dictated by the sequence of the polymorphic nucleotides in the template.

The fluorescently-tagged primer:template complex, still attached to the magnetic microspheres, is then separated from the reaction mix containing the unincorporated nucleotides by, for example, washing the magnetically immobilized beads in a suitable buffer. Additionally, it is desirable in some circumstances to then elute the primer from the immobilized template strand with NaOH, transfer the eluted primer to a separate medium or container, and subsequently determine the identity of the incorporated terminator. The identity of the attached fluorescent group is then assessed by illuminating the modified DNA strand with light, preferably provided by a laser, of a suitable wavelength and intensity and spectrophotometrically analyzing the emission spectrum produced. In general, for a two allele (diploid) system at any given site in the DNA sequence, there are ten possible canonical emission spectra produced, corresponding to the sixteen possible homozygotic and heterozygotic pairings. By suitable matching of the measured spectra to this library of canonical spectra it is possible to identify which chain-terminating nucleotide(s) have been added to the 3'-terminus of the primer and thereby identify the nature of the sequence polymorphism in the template. Spectra produced by multiple allele systems or by alleles present in a ratio other than 1:1 can also be deconvolved by suitable mathematical treatments to identify and estimate the relative ratios of each contributing nucleotide.

All of the above steps involve chemistries, manipulations, and protocols that have been, or are amenable to being, automated. Thereby, incorporation of the preferred mode of practice of this invention into the operation of a suitably programmed robotic workstation should result in significant cost savings and increases in productivity for virtually any diagnostic procedure that depends on the detection of specific nucleotide sequences or sequence differences in nucleic acids derived from biological samples.

What we claim is:

1. A method of determining the identity of a nucleotide base at a specific position in a nucleic acid of interest, which comprises:
   (a) treating a sample containing the nucleic acid of interest, if the nucleic acid is double-stranded, so as to obtain unpaired nucleotide bases spanning the specific position, or directly employing step (b) if the nucleic acid of interest is single-stranded;
   (b) contacting the sample from step (a), with an oligonucleotide primer which is fully complementary to and which hybridizes specifically to a stretch of nucleotide bases present in the nucleic acid of interest immediately adjacent to the nucleotide base to be identified, under high stringency hybridization conditions, so as to form a duplex between the primer and the nucleic acid of interest such that the nucleotide base to be identified is the first unpaired base in the template immediately downstream of the 3' end of the primer in said duplex; and
   (c) contacting the duplex from step (b), in the absence of dATP, dCTP, dGTP, or dTTP, with at least two different terminators of a nucleic acid template-dependent, primer extension reaction capable of specifically terminating the extension reaction in a manner strictly dependent upon the identity of the unpaired nucleotide base in the template immediately downstream of the 3' end of the primer wherein one of said terminators is complementary to said nucleotide base to be identified and wherein at least one of said terminators is labeled with a detectable marker; wherein said contacting is under conditions sufficient to permit base pairing of said complementary terminator with the nucleotide base to be identified and occurrence of a template-dependent primer extension reaction sufficient to incorporate said complementary terminator onto the 3' end of the primer to thereby extend said 3' end of said primer by one terminator;
   (d) determining the presence and identity of the nucleotide base at the specific position in the nucleic acid of interest by detecting the detectable marker of said incorporated terminator while said terminator is incorporated at the 3' end of the extended primer, and wherein said detection is conducted in the absence of non-terminator nucleotides.

2. The method of claim 1, wherein in step (c), the duplex from step (b) is contacted with four labeled terminators, wherein only one of the terminators has a detectable marker, and wherein in said method said step (c) is performed four times, with a different one of the four terminators being labelled.

3. The method of claim 1, wherein in step (c), the duplex from step (b) is contacted with four labeled terminators, each with a different detectable label.

4. A method of typing a sample containing nucleic acids which comprises identifying the nucleotide base or bases present at each of one or more specific positions, each such nucleotide base being identified using the method of claim 2 or 3, and each such specific position being determined using a different primer.

5. A method of claim 4, wherein the identity of each nucleotide base or bases at each position is determined individually or wherein the identities of the nucleotide bases at different positions are determined simultaneously.

6. A method for identifying different alleles in a sample containing nucleic acids which comprises identifying the nucleotide base or bases present at each of one or more specific positions, each such nucleotide base being identified by the method of claim 2 or 3.

7. A method for determining the genotype of an organism at one or more particular genetic loci which comprises:
   (a) obtaining from the organism a sample containing genomic DNA; and
   (b) identifying the nucleotide base or bases present at each of one or more specific positions in nucleic acids of interest, each such base or bases being identified using the method of claim 2 or 3, and thereby identifying different alleles and thereby, in turn, determining the genotype of the organism at one or more particular genetic loci.

8. A method of claim 2 or 3, wherein the conditions for the occurrence of the template-dependent, primer extension reaction in step (c) are created, in part, by the presence of a suitable template-dependent enzyme.

9. A method of claim 8, wherein the template-dependent enzyme is *E. coli* DNA polymerase I or the "Klenow fragment" thereof, T4 DNA polymerase, T7 DNA polymerase *T. aquaticus* DNA polymerase, a retroviral reverse transcriptase, or combinations thereof.

10. A method of claim 2 or 3, wherein the nucleic acid of interest is a deoxyribonucleic acid, a ribonucleic acid, or a copolymer of deoxyribonucleic acid and ribonucleic acid.

11. A method of claim 2 or 3, wherein the primer is an oligodeoxyribonucleotide, an oligoribonucleotide, or a copolymer of deoxyribonucleic acid and ribonucleic acid.

12. A method of claim 2 or 3, wherein the template is a deoxyribonucleic acid, the primer is an oligodeoxyribonucleotide, oligoribonucleotide, or a copolymer of deoxyribonucleotides and ribonucleotides, and the template-dependent enzyme is a DNA polymerase.

13. A method of claim 2 or 3, wherein the template is a ribonucleic acid, the primer is an oligodeoxyribonucleotide, oligoribonucleotide, or a copolymer of deoxyribonucleotides and ribonucleotides, and the template-dependent enzyme is a reverse transcriptase.

14. A method of claim 2 or 3, wherein the template is a deoxyribonucleic acid, the primer is an oligoribonucleotide, and the enzyme is an RNA polymerase.

15. A method of claim 2 or 3, wherein the template is a ribonucleic acid, the primer is an oligoribonucleotide, and the template-dependent enzyme is an RNA replicase.

16. A method of claim 2 or 3, wherein, prior to the primer extension reaction in step (c), the template has been capped at its 3' end by the addition of a terminator to the 3' end of the template, said terminator being capable of terminating a template-dependent, primer extension reaction.

17. A method of claim 16, wherein the terminator is a dideoxynucleotide.

18. A method of claim 2 or 3, wherein the nucleic acid of interest has been synthesized enzymatically in vivo, synthesized enzymatically in vitro, or synthesized non-enzymatically.

19. A method of claim 2 or 3, wherein the oligonucleotide primer has been synthesized enzymatically in vivo, synthesized enzymatically in vitro, or synthesized non-enzymatically.

20. A method of claim 2 or 3, wherein the oligonucleotide primer comprises one or more moieties that permit affinity separation of the primer from the unincorporated reagent and/or the nucleic acid of interest.

21. A method of claim 20, wherein the oligonucleotide primer comprises biotin which permits affinity separation of the primer from the unincorporated reagent and/or nucleic acid of interest via binding of the biotin to streptavidin which is attached to a solid support.

22. A method of claim 2 or 3, wherein the sequence of the oligonucleotide primer comprises a DNA sequence that permits affinity separation of the primer from the unincorporated reagent and/or the nucleic acid of interest via base pairing to a complementary sequence present in a nucleic acid attached to a solid support.

23. A method of claim 2 or 3, wherein the nucleic acid of interest comprises one or more moieties that permit affinity separation of the nucleic acid of interest from the unincorporated reagent and/or the primer.

24. A method of claim 23, wherein the nucleic acid of interest comprises biotin which permits affinity separation of the nucleic acid of interest from the unincorporated reagent and/or the primer via binding of the biotin to streptavidin which is attached to a solid support.

25. A method of claim 2 or 3, wherein the sequence of the nucleic acid of interest comprises a DNA sequence that permits affinity separation of the nucleic acid of interest from the unincorporated reagent and/or the primer via base pairing to a complementary sequence present in a nucleic acid attached to a solid support.

26. A method of claim 2 or 3, wherein the oligonucleotide primer is labeled with a detectable marker.

27. A method of claim 26, wherein the oligonucleotide primer is labeled with a detectable marker that is different from any detectable marker present in the reagent or attached to the nucleic acid of interest.

28. A method of claim 2 or 3, wherein the nucleic acid of interest is labeled with a detectable marker.

29. A method of claim 28, wherein the nucleic acid of interest is labeled with a detectable marker that is different from any detectable marker present in the reagent or attached to the primer.

30. A method of claim 2 or 3, wherein the nucleic acid of interest comprises non-natural nucleotide analogs.

31. A method of claim 30, wherein the non-natural nucleotide analogs comprise deoxyinosine or 7-deaza-2'-deoxyguanosine.

32. A method of claim 2 or 3, wherein the nucleic acid of interest has been synthesized by the polymerase chain reaction.

33. A method of claim 2 or 3, wherein the sample comprises genomic DNA from an organism, RNA transcripts thereof, or cDNA prepared from RNA transcripts thereof.

34. A method of claim 2 or 3, wherein the sample comprises extragenomic DNA from an organism, RNA transcripts thereof, or cDNA prepared from RNA transcripts thereof.

35. A method of claim 2 or 3, wherein the primer is separated from the nucleic acid of interest after the primer extension reaction in step (c) by using appropriate denaturing conditions.

36. A method of claim 35, wherein the denaturing conditions comprise heat, alkali, formamide, urea, glyoxal, enzymes, and combinations thereof.

37. A method of claim 36, wherein the denaturing conditions comprise treatment with 0.2N NaOH.

38. A method of claim 33, wherein the organism is a plant, microorganism, virus, or bird.

39. A method of claim 33, wherein the organism is a vertebrate or invertebrate.

40. A method of claim 33, wherein the organism is a mammal.

41. A method of claim 40, wherein the mammal is a human being.

42. A method of claim 40, wherein the mammal is a horse, dog, cow, cat, pig, or sheep.

43. A method of determining the presence or absence of a particular target nucleic acid molecule in a sample of nucleic acids, which comprises:

(a) treating the sample of nucleic acids, if such sample of nucleic acids contains double-stranded nucleic acids, so as to obtain single-stranded nucleic acids, or directly employing step (b) if the sample of nucleic acids contains only single-stranded nucleic acids;

(b) contacting the sample from step (a), with an oligonucleotide primer which is fully complementary to and which hybridizes specifically to a stretch of nucleotide bases present in said target nucleic acid molecule immediately adjacent to a preselected nucleotide base, under high stringency hybridization conditions so as to form a duplex between the primer and the nucleic acid of interest such that the preselected nucleotide base is the first unpaired base in the template immediately downstream of the 3' end of the primer in said duplex; and (c) contacting the duplex from step (b), in the absence of dATP, dCTP, dGTP, or dTTP, with at least two different terminators of a nucleic acid template-dependent, primer extension reaction capable of specifically terminating the extension reaction in a manner strictly dependent upon the identity of the unpaired nucleotide base in the template immediately downstream of the 3' end of the primer wherein one of said terminators is complementary to said nucleotide base to be identified and wherein at least one of said terminators is labeled with a detectable marker; wherein said contacting is under conditions sufficient to permit base pairing of said complementary terminator with said unpaired nucleotide base immediately downstream of the 3' end of said hybridized primer and occurrence of a template-dependent primer extension reaction sufficient to incorporate said complementary terminator onto the 3' end of the primer to thereby extend said 3' end of said primer by one terminator;

(d) determining the presence of the target nucleic acid molecule by detecting the detectable marker of said incorporated terminator while said terminator is incorporated at the 3' end of the extended primer, and wherein said detection is conducted in the absence of non-terminator nucleotides.

44. The method of claim 43, wherein in step (c), the duplex from step (b) is contacted with four labeled terminators, wherein only one of the terminators has a detectable marker, and wherein in said method said step (p) is performed four times, with a different one of the four terminators being labelled.

45. The method of claim 43, wherein in step (c), the duplex from step (b) is contacted with four labeled terminators, each with a different detectable label.

46. A method of determining the identity of a nucleotide base at a specific position in a nucleic acid of interest which comprises:

(a) (1) incubating a sample containing the nucleic acid of interest with at least two oligonucleotide primers, and a polymerase, said primers being sufficient to mediate a polymerase chain reaction amplification of said nucleic acid of interest, wherein said incubation is conducted under conditions sufficient to permit said amplification to occur;

(2) treating a sample containing said amplified nucleic acid of interest, if such nucleic acid is double-stranded, so as to obtain unpaired nucleotide bases spanning the specific position, or directly employing step (b) if the nucleic acid of interest is single-stranded;

(b) contacting the sample from step (a2), under hybridizing conditions, with an oligonucleotide primer which is fully complementary to and which hybridizes specifically to a stretch of nucleotide bases present in the nucleic acid of interest immediately adjacent to the nucleotide base to be identified, so as to form a duplex between the primer and the nucleic acid of interest such that the nucleotide base to be identified is the first unpaired base in the template immediately downstream of the 3' end of the primer in said duplex; and (c) contacting the duplex from step (b), in the absence of dATP, dCTP, dGTP, or dTTP, with at least two different terminators of a nucleic acid template-dependent, primer extension reaction capable of specifically terminating the extension reaction in a manner strictly dependent upon the identity of the unpaired nucleotide base in the template nucleic acid of interest immediately downstream of the 3' end of the primer wherein one of said terminators is complementary to said nucleotide base to be identified and wherein at least one of said terminators is labeled with a detectable marker, wherein said contacting is under conditions sufficient to permit base pairing of said complementary terminator with the nucleotide base to be identified and occurrence of a template-dependent primer extension reaction sufficient to incorporate said complementary terminator onto the 3' end of the primer to thereby extend said 3' end of said primer by one terminator;

(d) determining the presence and identity of the nucleotide base at the specific position in the nucleic acid of interest by detecting the detectable market of said incorporated terminator while said terminator is incorporated at the 3' end of the extended primer, and wherein said detection is conducted in the absence of non-terminator nucleotides.

47. A method of determining the presence or absence of a particular target nucleic acid molecule in a sample of nucleic acids which comprises:

(a) (1) incubating said sample of nucleic acids with at least two oligonucleotide primers, and a polymerase, said primers being sufficient to mediate a polymerase chain reaction amplification of said desired polynucleotide if said desired polynucleotide is present in said sample, wherein said incubation is conducted under conditions sufficient to permit said amplification to occur;

(2) treating said incubated sample of nucleic acids, if such sample of nucleic acids contains double-stranded nucleic acids, so as to obtain single-stranded nucleic acids, or directly employing step (b) if the sample of nucleic acids contains only double-stranded nucleic acids;

(b) contacting the sample from step (a2), under hybridizing conditions, with an oligonucleotide primer which is fully complementary to and which hybridizes specifically to a stretch of nucleotide bases present in said target nucleic acid molecule immediately adjacent to a preselected nucleotide base, so as to form a duplex between the primer and the nucleic acid of interest such that the preselected nucleotide base is the first unpaired base in the template immediately downstream of the 3' end of the primer in said duplex; and (c) contacting the duplex from step (b), in the absence of dATP, dCTP, dGTP, or dTTP, with at least two different terminators of a nucleic acid template-dependent, primer extension reaction capable of specifically terminating the extension reaction in a manner strictly dependent upon the identity of the unpaired nucleotide base in the template immediately downstream of the 3' end of the primer wherein one of said terminators is complementary to said nucleotide base to be identified and wherein at least one of said terminators is labeled with a detectable marker; wherein said contacting is under conditions sufficient to permit base pairing of said complementary terminator with said unpaired nucleotide base immediately downstream of the 3' end of said hybridized primer and occurrence of a template-dependent, primer extension reaction sufficient to incorporate said complementary terminator onto the 3' end of the primer to thereby extend said 3' end of said primer by one terminator; and (d) determining the presence of the target nucleic acid molecule by detecting the detectable marker of said incorporated terminator while said terminator is incorporated at the 3' end of the extended primer, and wherein said detection is conducted in the absence of non-terminator nucleotides.

48. A method of typing a sample containing nucleic acids which comprises determining the presence or absence of one or more particular nucleotide sequences, the presence or absence of each such nucleotide sequence being determined by the method of claim 40 or 47.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: Other nucleic acid ( x i ) SEQUENCE DESCRIPTION: SEQ ID NO:1:

GCCTTGGCGT TGTAGAA                                                                                              17

( 2 ) INFORMATION FOR SEQ ID NO:2:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: Other nucleic acid ( i x ) FEATURE:
      ( A ) NAME/KEY: modified_base
      ( B ) LOCATION:
      ( D ) OTHER INFORMATION: /note= "5'terminus biotinylated
            using biotin- XX-NHS ester, a derivative of
            biotin-N- hydroxysuccinimide, from Clontech ( x i ) SEQUENCE DESCRIPTION: SEQ ID NO:2:

ATCAGATACT TCTACAACGC CAAGGCTGGG CT                                                                             32

( 2 ) INFORMATION FOR SEQ ID NO:3:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: Other nucleic acid ( i x ) FEATURE:
      ( A ) NAME/KEY: modified_base
      ( B ) LOCATION:
      ( D ) OTHER INFORMATION: /note= "5'terminus biotinylated
            using biotin- XX-NHS ester, a derivative of
            biotin-N- hydroxysuccinimide, from Clontech ( x i ) SEQUENCE DESCRIPTION: SEQ ID NO:3:

ATCAGATATT TCTACAACGC CAAGGCTGGG CT                                                                             32

( 2 ) INFORMATION FOR SEQ ID NO:4:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: Other nucleic acid ( x i ) SEQUENCE DESCRIPTION: SEQ ID NO:4:

TGTTTTGCAC AAAAGCA                                                                                              17

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:5:

GTTTTGCACA AAAGCAT                                  17

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid ( i x ) FEATURE:
        ( A ) NAME/KEY: modified_base
        ( B ) LOCATION:
        ( D ) OTHER INFORMATION: /note= "5'terminus biotinylated
            using Midland Certified Reagent Company's Biotin
            dX reagent, a biotin derivative phosphoramidite."

( x i ) SEQUENCE DESCRIPTION: SEQ ID NO:6:

AGGATGCTTT TGTGCAAAAC AC                          22

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid ( i x ) FEATURE:
        ( A ) NAME/KEY: modified_base
        ( B ) LOCATION:
        ( D ) OTHER INFORMATION: /note= "5'terminus biotinylated
            using biotin- XX-NHS ester, a derivative of
            biotin-N- hydroxysuccinimide, from Clontech ( x i ) SEQUENCE DESCRIPTION: SEQ ID NO:7:

AGATGATGCT TTTGTGCAAA ACAC                        24

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:8:

TCAATACCTG AGTCCCGACA CCCTG                       25

( 2 ) INFORMATION FOR SEQ ID NO:9:

( i ) SEQUENCE CHARACTERISTICS:
        ( A ) LENGTH: 25 base pairs ( B ) TYPE: nucleic acid
            ( C ) STRANDEDNESS: single
            ( D ) TOPOLOGY: linear ( i i ) MOLECULE TYPE: Other nucleic acid ( x i ) SEQUENCE DESCRIPTION: SEQ ID NO:9:

AGCCTCAGAC CGCGTGGTGC CTGGT                                                                 25

( 2 ) INFORMATION FOR SEQ ID NO:10:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: Other nucleic acid ( x i ) SEQUENCE DESCRIPTION: SEQ ID NO:10:

TTCTTCTTGC ATCTATGTTC G                                                                     21

( 2 ) INFORMATION FOR SEQ ID NO:11:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: Other nucleic acid ( x i ) SEQUENCE DESCRIPTION: SEQ ID NO:11:

TTAAGCACCA CCACAGGTCC T                                                                     21

( 2 ) INFORMATION FOR SEQ ID NO:12:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: Other nucleic acid ( x i ) SEQUENCE DESCRIPTION: SEQ ID NO:12:

AGAGAAACAA TTTCAAG                                                                          17

( 2 ) INFORMATION FOR SEQ ID NO:13:

( i ) SEQUENCE CHARACTERISTICS:
            ( A ) LENGTH: 240 base pairs
            ( B ) TYPE: nucleic acid
            ( C ) STRANDEDNESS: double
            ( D ) TOPOLOGY: linear ( i i ) MOLECULE TYPE: DNA (genomic)

( x i ) SEQUENCE DESCRIPTION: SEQ ID NO:13:

TTTCTTCTTG CATCTATGTT CGTTTTTTCT ATTGCTACAA ATGCCTATGC ACGGCCTGAC             60

TTCTGCCTAG AGCCTCCATA TACGGGTCCC TGCAAGGCCA GAATTATCAG ATAYTTCTAC           120

AACGCCAAGG CTGGGCTCTG CCAGACCTTT GTATATGGTG GCTGCAGAGC TAAGAGAAAC           180

AATTTCAAGR GCGCAGAGGA CTGCATGAGG ACCTGTGGTG GTGCTTAAGG GCCCCGGGAA           240

( 2 ) INFORMATION FOR SEQ ID NO:14:

( i ) SEQUENCE CHARACTERISTICS:

(A) LENGTH: 327 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:14:

| | | | | | | |
|---|---|---|---|---|---|---|
| AGATGATGCT | TTTGTGCAAA | ACACTTTTA  | ACACCTCTTT | TAAAATTTCT | TTCAAATTCT | 60 |
| ACGGCATTTT | TTTCCTGAAA | ATGCTTCGGT | TTTAGGTCAA | AGCTTTATTC | TCCTAAGAAC | 120 |
| CTAACTCCCA | CTGGTCTCAG | GCGCCCTCTC | GGAGCCCTCG | GGGAGTCTTT | GCCCCCCAAT | 180 |
| CTTGGCATTC | TCCCCTGACA | CTCGCCCAAG | GCCCTAACC  | TGCACCCGGG | CACCAGGCAC | 240 |
| CACGCGGTCT | GAGGCTTCAG | CAGGGAAGGC | CTGCTCTCCG | TTCACACTGC | TTTCAGGCCC | 300 |
| GGCAGGGTGT | CGGGACTCAG | GTATTGA    |            |            |            | 327 |

(2) INFORMATION FOR SEQ ID NO:15:

(i) SEQUENCE CHARACTERISTICS:
        (A) LENGTH: 328 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:15:

| | | | | | | |
|---|---|---|---|---|---|---|
| AGATGATGCT | TTTGTGCAAA | ACACTTTTA  | ACACCTCTTT | TAAAATTTCT | TTCAAATTCT | 60 |
| ACGGCATTTT | TTTCCTGAAA | ATGCTTCGGT | TTTAGGTCAA | AGCTTTATTC | TCCTAAGAAC | 120 |
| CTAACTCCCA | CTGGTCTCAG | GCGCCCTCTC | GGAGCCCTCG | GGGAGTCTTT | GCCCCCCAAT | 180 |
| CTTGGCATTC | TCCCCTGACA | CTCGCCCAAG | GCCCTAACC  | TGCACCCGGG | GAACCAGGCA | 240 |
| CCACGCGGTC | TGAGGCTTCA | GTAGGCAAGG | CCTGCTCTCC | GTTCACACTG | CTTTCAGGCC | 300 |
| CGGCAGGGTG | TCGGGACTCA | GGTATTGA   |            |            |            | 328 |